United States Patent
Laboureau et al.

(10) Patent No.: US 8,445,459 B2
(45) Date of Patent: May 21, 2013

(54) COMBINATION OF MONOSACCHARIDE WITH C-GLYCOSIDE DERIVATIVE AND USE THEREOF

(75) Inventors: Julien Laboureau, Issy les Moulineaux (FR); Jean-Thierry Simonnet, Cachan (FR); Pascal Portes, Nogent sur Marne (FR)

(73) Assignee: L'Oreal, Paris (FR)

( * ) Notice: Subject to any disclaimer, the term of this patent is extended or adjusted under 35 U.S.C. 154(b) by 428 days.

(21) Appl. No.: 12/649,366

(22) Filed: Dec. 30, 2009

(65) Prior Publication Data

US 2010/0168055 A1    Jul. 1, 2010

Related U.S. Application Data

(60) Provisional application No. 61/144,754, filed on Jan. 15, 2009.

(30) Foreign Application Priority Data

Dec. 30, 2008  (FR) ..................... 08 59150

(51) Int. Cl.
*A61K 8/60* (2006.01)
*A61Q 19/00* (2006.01)

(52) U.S. Cl.
USPC .............................. 514/53; 514/23

(58) Field of Classification Search
USPC .................................... 514/23, 53
See application file for complete search history.

(56) References Cited

U.S. PATENT DOCUMENTS

| | | | |
|---|---|---|---|
| 4,252,951 A * | 2/1981 | Jackson et al. | 540/220 |
| 5,789,385 A * | 8/1998 | Anderson et al. | 514/25 |
| 7,049,300 B2 * | 5/2006 | Dalko et al. | 514/23 |
| 2003/0044439 A1 * | 3/2003 | Dobson et al. | 424/401 |

FOREIGN PATENT DOCUMENTS

| | | |
|---|---|---|
| EP | 1 589 010 | 10/2005 |
| FR | 2 609 397 | 7/1988 |
| FR | 2 756 735 | 6/1998 |
| FR | 2 768 623 | 3/1999 |
| FR | 2 773 324 | 7/1999 |
| FR | 2 876 283 | 4/2006 |
| FR | 2876283 | * 4/2006 |
| WO | WO 02/051828 | 7/2002 |
| WO | WO 2008/148966 | 12/2008 |
| WO | WO 2009/034559 | 3/2009 |

OTHER PUBLICATIONS

Braga, Chem. Comm. 2005, 29, 3635-3645.*
U.S. Appl. No. 12/648,485, filed Dec. 29, 2009, Simonnet, et al.
U.S. Appl. No. 12/649,367, filed Dec. 30, 2009, Laboureau, et al.
U.S. Appl. No. 12/649,372, filed Dec. 30, 2009, Laboureau, et al.
U.S. Appl. No. 12/649,370, filed Dec. 30, 2009, Laboureau, et al.
U.S. Appl. No. 12/649,415, filed Dec. 30, 2009, Laboureau, et al.
U.S. Appl. No. 12/649,368, filed Dec. 30, 2009, Laboureau, et al.

* cited by examiner

*Primary Examiner* — Shaojia Anna Jiang
*Assistant Examiner* — Ganapathy Krishnan
(74) *Attorney, Agent, or Firm* — Oblon, Spivak, McClelland, Maier & Neustadt, L.L.P.

(57) ABSTRACT

Composition, especially a cosmetic and/or dermatological composition, containing, in a physiologically acceptable medium, at least one of mannose, and rhamnose and at least one additional compound chosen from C-glycosides and C-glycoside derivatives. Use of such a composition, and also a device containing it.

18 Claims, 3 Drawing Sheets

COMBINATION OF MONOSACCHARIDE WITH C-GLYCOSIDE DERIVATIVE AND USE THEREOF

REFERENCE TO PRIOR APPLICATIONS

This application claims priority to U.S. provisional application Ser. No. 61/144,754, filed Jan. 15, 2009; and to French patent application 08 59150, filed Dec. 30, 2008, both incorporated herein by reference.

FIELD OF THE INVENTION

The present invention relates to a composition, especially a cosmetic and/or dermatological composition, comprising, in a physiologically acceptable medium, a combination of at least one monosaccharide selected from mannose, rhamnose and a mixture thereof, and of at least one additional compound selected from C-glycosides and derivatives thereof, and mixtures thereof. The present invention also relates to the use of such a composition, and to a device containing it.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Human skin is made up mainly of two main layers, namely the dermis and the epidermis that superficially covers the dermis. The dermis provides the epidermis with a solid support. It is also its nourishing element. It is made up mainly of fibroblasts and an extracellular matrix composed mainly of collagen, elastin and a substance known as ground substance. These components are synthesized by the fibroblasts.

The cohesion between the epidermis and the dermis is provided by the dermo-epidermal junction. This is a complex region about 100 nm thick, which comprises the basal pole of the basal keratinocytes, the epidermal membrane and the sub-basal zone of the superficial dermis. From a structural viewpoint, hemidesmosomes, into which are inserted keratin filaments (hemidesmosome-tonofilament complex) are distributed on the plasma membrane of the basal keratinocytes. Facing these hemidesmosome-tonofilament complexes are anchoring filaments that cross the epidermal basal membrane. The anchoring filaments are attached to laminin V on the epidermal side. It has been shown that these anchoring fibrils, which are entirely visible by electron microscopy, are composed of type VII collagen (referred to as collagen VII hereinbelow). The collagen VII is synthesized by keratinocytes and fibroblasts, but more substantially by keratinocytes (Aumailley M., Rousselle P. Laminins of the dermoepidermal junction. Matrix Biology, 1999, 18: 19-28; Nievers M., Schaapveld R., Sonnenberg A. Biology and function of hemidesmosomes. Matrix Biology, 1999, 18: 5-17).

Collagens are the major proteins of the extracellular matrices of the skin. To date, 20 types of collagen have been identified, and are noted from I to XX. Collagens are not all synthesized by the same cell types, regulation of their expression differs from one collagen to another, and all collagen molecules are variants of a common precursor, which is the α chain of procollagen.

The dermoepidermal junction is a structure that conditions the surface state of the skin. Thus, a dermoepidermal junction with intact anchoring structures is maintained folded, thus making it possible to increase the surface area of the contact zone between the dermis and the epidermis, to promote exchanges of diffusible factors, especially between these two tissues, to reinforce their cohesion and to improve the appearance of the epidermis. In cases where the anchoring structures are impaired, in particular due to a deficiency in the synthesis of collagen IV, collagen VII or laminin V and/or due to aging, this causes flattening of the dermoepidermal junction. Fewer exchanges take place, the two tissues are less solidly connected, the epidermis folds, and, as the skin is less firm and less taut, wrinkles appear and the fragility of the skin with respect to mechanical attack is increased.

With age, collagen becomes thinner and disorganised, the renewal of the skin cells decreases, wrinkles appear on the surface of the skin, and the skin is duller and less firm. Cutaneous aging is conditioned by genetic factors. Moreover, certain environmental factors such as smoking and especially exposure to sunlight accelerate it. The skin thus has a much more aged appearance on the areas exposed to sunlight, such as the back of the hands or the face. Thus, these other factors also have a negative impact on the natural collagen of the skin.

Consequently, given the important role of collagen in the integrity of the skin and in its resistance to external attacking factors of mechanical type, stimulation of the synthesis of these collagens, and in particular of procollagen I, collagen IV, collagen VII and laminin V, appears to be an effective means for overcoming the signs of aging of the skin.

To overcome the abovementioned drawbacks, to improve the appearance of the skin, to improve its mechanical properties and to avoid the pathologies associated with cell deficiency, deficiency of cell renewal or deficiency of certain compounds of the dermis or of the dermoepidermal junction, the inventors view it to be important to develop products that are aimed at reinforcing or maintaining the role as a support and a nourishing factor played by the dermis, the cohesion between the various layers of the skin, and more particularly the cohesion between the dermis and the epidermis, by increasing keratinocyte proliferation, by stimulating fibroblast proliferation and metabolism and by stimulating the synthesis of collagens, in particular of procollagen I, collagen IV, collagen VII and laminin V.

The epidermis, which covers the dermis and is in direct contact with the external environment, has the main role of protecting the body against the dehydration and external attack. Natural human epidermis is composed mainly of three types of cell, namely keratinocytes, which form the vast majority, melanocytes and Langerhans cells. Each of these cell types contributes, by virtue of its intrinsic functions, towards the essential role played in the body by the skin.

The dermis is made up mainly of fibroblasts and an extracellular matrix. Leucocytes, mastocytes and tissue macrophages are also found therein. It is also made up of blood vessels and nerve fibres.

The extracellular matrix of the dermis, like that of all the connective tissues of the body, is composed of proteins belonging to several major families: collagens, matrix glycoproteins other than collagens (fibronectin, laminin), elastin and proteoglycans. Glycosaminoglycans in free form (i.e. not bound to a protein) are also found in the extracellular matrix of the dermis, as in all connective tissues of the body.

It is now well established that specific interactions exist between these various classes of proteins to give rise to a functional tissue.

Proteoglycans are complex macromolecules formed from a branched central protein trunk, or protein network, to which are attached numerous polysaccharide side chains known as glycosaminoglycans.

In the rest of the present patent application, proteoglycans will be denoted by the abbreviation PG and glycosaminoglycans by the abbreviation GAG.

GAGs were for a long time referred to as acidic mucopolysaccharides on account of their high water-retaining capacity, their carbohydrate nature and their acidic nature originating from their multiple negative charges.

Thus, the polarity of GAGs makes them implicitly participate in certain biological functions such as the hydration of tissues, the binding of cations or the barrier role of ionic filtration.

PGs and GAGs are synthesized by various cells in the dermis and the epidermis: fibroblasts, keratinocytes and melanocytes.

The fibroblasts mainly synthesize collagens, matrix glycoproteins other than collagens (fibronectin, laminin), proteoglycans and elastin. The keratinocytes mainly synthesize sulfated GAGs and hyaluronic acid, while the melanocytes apparently do not produce any hyaluronic acid.

When they are incorporated in a PG, GAGs are linear chains composed of a repetition of a base diholoside always containing a hexosamine (glucosamine or galactosamine) and another saccharide (glucuronic acid, iduronic acid or galactose). The glucosamine is either N-sulfated or N-acetylated. On the other hand, the galactosamine is always N-acetylated. In addition, there may be sulfates O-bonded to the hexosamine, uronic acid and galactose.

The strong anionic nature of GAGs is explained by the presence of carboxylate groups in the hexuronic acids (glucuronic acid and iduronic acid) and of O- and N-bonded sulfate groups.

The main GAGs are hyaluronic acid or hyaluronan (HA), heparan sulfate (HS), heparin (HP), chondroitin, chondroitin sulfate (CS), chondroitin 4-sulfate or chondroitin sulfate A (CSA), chondroitin 6-sulfate or chondroitin sulfate C (CSC), dermatan sulfate or chondroitin sulfate B (CSB) and keratan sulfate (KS), which differs from the other glycosaminoglycans by the presence of galactose instead of uronic acid.

When they are combined with a protein in the form of PG, the GAGs are linked via anchoring structures to the various polypeptide chains, named the "core" protein or carrier protein, and thus form PG molecules.

GAGs may also exist in the extracellular matrix in free form, ie not bound to a matrix protein: this is especially the case for hyaluronic acid.

During the synthesis of PGs, the GAGs are polymerized from these anchoring structures.

The synthesis of GAGs requires the coordinated and concerted action of very specific enzymes (transferases, epimerases and sulfotransferases) that are adjacent in the membrane of the endoplasmic reticulum and of the golgi bodies. Next, a multitude of biochemical reactions (N-deacetylation, N- and O-sulfation, and epimerization) modify the two constituent saccharides of the base unit, heterogeneously along the chain. For example, from one heparan sulfate chain to another, the glucuronic acid/iduronic acid ratio, the nature, number and position of the O-sulfations, and the N-sulfate/O-sulfate ratio may vary, which essentially offers immense structural diversity.

In general, the biological roles of PGs are highly diversified, ranging from a passive mechanical support function (for example serglycines) or an ionic barrier role in molecular filtration (for example perlecane and bamacane of the glomerular basal membrane), to more specific effects in cell adhesion, spreading, proliferation and differentiation or morphogenesis, or to highly specific effects of PG-protein interactions, such as the beta-glycan receptor function or the interaction of decorin with collagen.

One of the roles of dermal connective tissue is to protect the body against external attack when simultaneously forming an informative interface.

To do this, the dermis has high mechanical strength while maintaining, however, great flexibility.

Its strength is ensured by the dense network of collagen fibres, but it is the PGs and the hyaluronic acid which, by ensuring the moisturization, distribution and suppleness of the fibres, make the difference between the skin and, for example, leather.

The PGs constitute 0.5% to 2% of the dry weight of the dermis, collagen alone representing up to 80% of this weight.

The concentration and distribution in human skin of GAGs and PGs vary with age.

Hyaluronic acid or hyaluronan (HA) is the main GAG of the dermis, the latter containing half the HA of the body.

The synthesis of HA is performed especially by the fibroblasts, close to the inner face of the plasma membrane. It is performed continuously. This gigantic polysaccharide (several million daltons) has a very high intrinsic viscosity, ensuring the moisturization and assembly of the various components of the connective tissue by forming supramolecular complexes.

Dermatan sulfate (DS), which was first isolated from the dermis, is also widely abundant in the skin. It constitutes 40% to 50% of the dermal GAGs.

In parallel with the mechanisms contributing to the development of these specialized extracellular matrices, continuous remodeling processes exist, the regulation of which depends on the balance between the synthesis and degradation of the protein components of the matrix.

Several families of matrix proteases are now described, as are the factors involved in their activation-inactivation.

In the course of chronological and/or actinic aging, the dermis and the epidermis undergo several changes and degradations which are reflected, with age, by flaccidness and a loss of suppleness of the skin.

Among the components degraded (especially collagen and elastin), the PGs and GAGs are also adversely affected. Specifically, over the course of aging, the fibroblasts and keratinocytes produce less and less PGs and GAGs and their synthesis is imperfect. This results in considerable disorganization: the deposition of GAGs on the protein skeleton forming the PG is abnormal, the consequence of this is a reduced avidity for water of these PGs thus a reduction in the moisturization and tonicity of tissues.

Restoring a normal production of PGs and GAGs by fibroblasts and keratinocytes contributes partially towards compensating for the loss of moisturization of the skin.

The degradation of these matrices thus contributes towards the phenomenon of dryness and of loss of suppleness of the skin.

The importance of having available products whose effects are directed towards maintaining the level of PGs and GAGs in the skin and thus of maintaining, inter alia, good moisturization and good suppleness of the skin, effectively combating the signs of aging, may thus be appreciated.

DETAILED DESCRIPTION OF THE PREFERRED EMBODIMENTS

Figure 1:
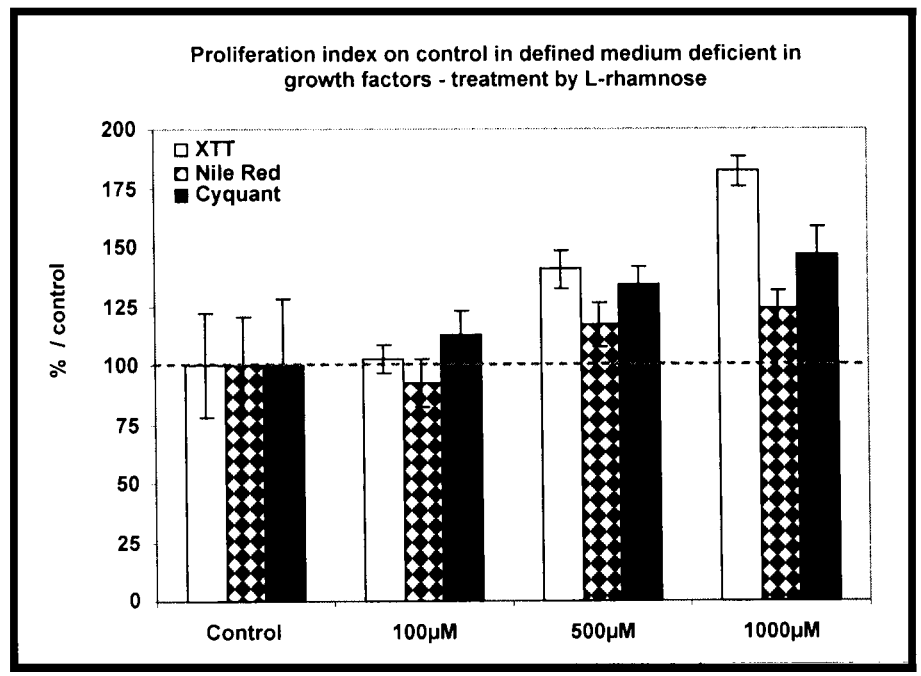
FIG. 1 shows the results obtained for the keratinocyte proliferation under certain conditions, described in more detail below. The values reported on the y-axis correspond to the percentages of labelled cells measured relative to the control.

In this regard, it has now been discovered, surprisingly and unexpectedly, that a combination of at least one monosaccharide chosen from mannose, rhamnose and a mixture thereof, and of at least one additional compound chosen from C-glycosides, derivatives thereof and mixtures thereof, produces a complementarity of action both on increasing the thickness of the epidermis, on reinforcing the structure of the dermoepidermal junction, in particular by increasing the synthesis of collagen IV and VII and/or laminins such as laminins V, and/or on stimulating the synthesis of procollagen I, and also on activating the proliferation of keratinocytes and/or fibroblasts. The complementarity of action of the combination according to the invention stimulates the synthesis of GAGs containing a D-glucosamine and/or N-acetyl-d-glucosamine residue, advantageously hyaluronic acid, and/or of PGs, advantageously proteoglycans containing hyaluronic acid, by the fibroblasts and/or keratinocytes, the metabolism and proliferation of which are also stimulated. The effect obtained with the combination defined above thus gives rise to skin regeneration acting both on the epidermis, the dermoepidermal junction and on the dermis, thus demonstrating overall anti-aging activity. In particular, the combination of monosaccharide according to the invention with a C-glycoside makes it possible to obtain an effect both on the cells and on the matrix surrounding them. Thus, this combination permits both fibroblasts stimulation and/or proliferation, and an increased production of glycosaminoglycans, which improves the extracellular matrix.

The invention demonstrates the activation and proliferation of keratinocytes and fibroblasts and the stimulation of procollagen I synthesis by mannose or rhamnose. The use of compositions containing them thus makes it possible to combat the signs of aging of the skin, and in particular age-related epidermal and/or dermal atrophy.

The use of these monosaccharides for the direct biological effects outlined above was hitherto unknown. However, patent application WO 2007/128939 mentions anti-aging activity obtained via a biomechanical effect of a tensioning agent in combination with saccharide compounds, which make it possible to increase the expression of the skin cell mechanoreceptors. This increase in the expression of mechanoreceptors is described as increasing the sensitization of skin cells to respond to the effects of tensioning agents.

Patent application WO 2005/063194 describes a galenical base with very high tolerance especially comprising mannose or rhamnose. It is specified that such a galenical base can function only in combination with an active agent of which it is only the vehicle. The dermal and/or cosmetic galenical bases disclosed are based essentially on the presence of the two polyols, namely mannitol and xylitol.

Moreover, the influence of C-glycosides on the synthesis of GAGs and PGs is described in patent application WO 2002/051828. The said document also describes the influence of C-glycosides on improving the three-dimensional structure of the dermoepidermal junction, which afford at this level reinforcement of the connection between laminins VI and nidogen, with, in particular, action on collagen IV.

The influence of certain C-xyloside derivatives on the synthesis of GAGs and on regulation of the expression of certain molecules of the dermoepidermal junction is known from the literature (Eur. J. Dermatol., 2008, 18(1), 36-40 and Eur. J. Dermatol., 2008, 18(2), 297-302).

The present invention thus relates in one embodiment to a composition, especially a cosmetic and/or dermatological composition, comprising a combination of at least one monosaccharide chosen from mannose, rhamnose and a mixture thereof, with at least one additional compound chosen from C-glycosides, derivatives thereof (C-glycoside derivatives) and mixtures thereof.

Mannose is a hexose that is the C2 epimer of glucose. Rhamnose (or 6-deoxymannose) formally constitutes the product of deoxygenation of mannose at C6. The monosaccharides according to the invention are in the D or L form of mannose and/or rhamnose or a mixture thereof, each form itself possibly being the alpha and/or beta anomer. The forms that are preferred according to the invention are D-mannose and/or L-rhamnose.

D-Mannose is present in plants, in particular certain fruit, including cranberries, or in hardwood (beech and birch). Rhamnose is found in nature in L form. D-Mannose and L-rhamnose are commercially available, for example from the company Danisco Sweeteners®.

In the present invention, the monosaccharide is preferably present as a monomer.

Preferably, the composition according to the invention comprises at least one C-glycoside corresponding to formula (I) below:

(I)

in which:

R represents:

a saturated $C_1$-$C_{20}$ and in particular $C_1$-$C_{10}$ or unsaturated $C_2$-$C_{20}$ and in particular $C_2$-$C_{10}$ linear alkyl radical, or a saturated or unsaturated, branched or cyclic $C_3$-$C_{20}$ and in particular $C_3$-$C_{10}$ alkyl radical;

a saturated $C_1$-$C_{20}$ and in particular $C_1$-$C_{10}$ or unsaturated $C_2$-$C_{20}$ and in particular $C_2$-$C_{10}$ linear, or saturated or unsaturated, branched or cyclic $C_3$-$C_{20}$ and in particular $C_3$-$C_{10}$ hydrofluoroalkyl or perfluoroalkyl radical; the hydrocarbon-based chain constituting said radicals possibly being, where appropriate, interrupted with 1, 2, 3 or more heteroatoms chosen from:

an oxygen, a sulfur, a nitrogen, and a silicon, and possibly being optionally substituted with at least one radical chosen from:
—$OR_4$,
—$SR_4$,
—$NR_4R_5$,
—$COOR_4$,
—$CONHR_4$,
—CN,
a halogen atom,
a $C_1$-$C_6$ hydrofluoroalkyl or perfluoroalkyl radical, and/or
a $C_3$-$C_8$ cycloalkyl radical,
with $R_4$ and $R_5$ possibly representing, independently of each other, a hydrogen atom or a saturated $C_1$-$C_{30}$ and in particular $C_1$-$C_{12}$ or unsaturated $C_2$-$C_{30}$ and in particular $C_2$-$C_{12}$ linear, or a saturated or unsaturated, branched or cyclic $C_3$-$C_{30}$ and in particular $C_3$-$C_{12}$ alkyl, perfluoroalkyl or hydrofluoroalkyl radical; or a $C_6$-$C_{10}$ aryl radical,
X represents a radical chosen from the groups:

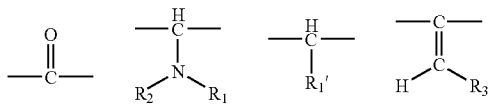

with $R_1$, $R_2$ and $R_3$ representing, independently of each other, a hydrogen atom or a radical R, with R as defined above, and $R'_1$ represents a hydrogen atom, an —OH group or a radical R as defined above, $R_1$ possibly also denoting a $C_6$-$C_{10}$ aryl radical;
S represents a monosaccharide or a polysaccharide comprising up to 20 sugar units and in particular up to 6 sugar units, in pyranose and/or furanose form and of L and/or D series, said mono- or polysaccharide possibly being substituted with a mandatorily free hydroxyl group, and optionally one or more optionally protected amine function(s), and
the bond S—$CH_2$—X represents a bond of C-anomeric nature, which may be α or β,
and also the cosmetically acceptable salts thereof, the solvates thereof such as hydrates, and the isomers thereof.

In the context of the present invention, the term "halogen" means chlorine, fluorine, bromine or iodine.

The term "aryl" denotes an aromatic ring such as phenyl, optionally substituted with one or more $C_1$-$C_4$ alkyl radicals.

The term "$C_3$-$C_8$ cycloalkyl" denotes an aliphatic ring containing from 3 to 8 carbon atoms, for example including cyclopropyl, cyclopentyl and cyclohexyl.

Among the alkyl groups that are suitable for use in the invention, mention may be made especially of methyl, ethyl, isopropyl, n-propyl, n-butyl, t-butyl, isobutyl, sec-butyl, pentyl, n-hexyl, cyclopropyl, cyclopentyl, cyclohexyl and allyl groups.

According to one embodiment of the invention, it is possible to use at least one C-glycoside derivative corresponding to formula (I) for which S may represent a monosaccharide or a polysaccharide containing up to 6 sugar units, in pyranose and/or furanose form and of L and/or D series, said monosaccharide or polysaccharide containing at least one hydroxyl function that is mandatorily free and/or optionally one or more amine functions that are mandatorily protected, X and R otherwise retaining all the definitions given above.

Advantageously, at least one monosaccharide of the invention may be chosen from D-glucose, D-galactose, D-mannose, D-xylose, D-lyxose, L-fucose, L-arabinose, L-rhamnose, D-glucuronic acid, D-galacturonic acid, D-iduronic acid, N-acetyl-D-glucosamine and N-acetyl-D-galactosamine, and advantageously denotes D-glucose, D-xylose, N-acetyl-D-glucosamine or L-fucose, and in particular D-xylose.

More particularly, a polysaccharide of the invention containing up to 6 sugar units may be chosen from one or more of D-maltose, D-lactose, D-cellobiose, D-maltotriose, a disaccharide combining a uronic acid chosen from D-iduronic acid and D-glucuronic acid with a hexosamine chosen from D-galactosamine, D-glucosamine, N-acetyl-D-galactosamine and N-acetyl-D-glucosamine, an oligosaccharide containing at least one xylose advantageously chosen from xylobiose, methyl-β-xylobioside, xylotriose, xylotetraose, xylopentaose and xylohexaose and especially xylobiose, which is composed of two xylose molecules linked via a 1-4 bond.

More particularly, S may represent a monosaccharide chosen from D-glucose, D-xylose, L-fucose, D-galactose and D-maltose, especially D-xylose. According to another embodiment of the invention, it is possible to use C-glycoside derivatives corresponding to formula (I) for which X represents a group chosen from —CO—, —CH(OH)—, —CH($NR_1R_2$)— and —CH(R)—, in particular —CO—, —CH(OH)—, —$CH(NH_2)$—, —$CH(NHCH_2CH_2CH_2OH)$—, —CH(NHPh)- and —$CH(CH_3)$—, and more particularly a —CO—, —CH(OH)— or —$CH(NH_2)$— group, and preferentially a —CH(OH)— group, S and R otherwise conserving all of the definitions given above.

According to another embodiment of the invention, it is possible to use at least one C-glycoside derivative corresponding to formula (I) for which R represents a saturated $C_1$-$C_{20}$ and in particular $C_1$-$C_{10}$ or unsaturated $C_2$-$C_{20}$ and in particular $C_2$-$C_{10}$ linear alkyl radical, or a saturated or unsaturated, branched or cyclic $C_3$-$C_{20}$ and in particular $C_3$-$C_{10}$ alkyl radical; and optionally substituted as described above, S and X otherwise conserving all the definitions given above.
Preferably, R denotes a linear $C_1$-$C_4$ and especially $C_1$-$C_3$ radical optionally substituted with —OH, —COOH or —$COOR''_2$, $R''_2$ being a saturated $C_1$-$C_4$ alkyl radical, especially ethyl.

Preferentially, R denotes an unsubstituted linear $C_1$-$C_4$ and especially $C_1$-$C_2$ alkyl radical, in particular ethyl.

Among the C-glycoside derivatives of formula (I) that are preferably used are those for which:
R represents a saturated $C_1$-$C_{20}$ and in particular $C_1$-$C_{10}$ or unsaturated $C_2$-$C_{20}$ and in particular $C_2$-$C_{10}$ linear alkyl radical, or a saturated or unsaturated, branched or cyclic $C_3$-$C_{20}$ and in particular $C_3$-$C_{10}$ alkyl radical, optionally substituted as described above;
S represents a monosaccharide as described above;
X represents —CO—, —CH(OH)—, —CH($NR_1R_2$)— or —CH(R)—, as defined above.

Preferably, a C-glycoside derivative of formula (I) is used, for which:
R denotes a linear $C_1$-$C_4$ and especially $C_1$-$C_3$ radical, optionally substituted with —OH, —COOH or —$COOR''_2$, $R''_2$ being a saturated $C_1$-$C_4$ alkyl radical, especially ethyl;
S represents a monosaccharide as described above;
X represents a group chosen from —CO—, —CH(OH)—, —$CH(NH_2)$—, —$CH(NHCH_2CH_2CH_2OH)$—, —CH(NHPh)- and —$CH(CH_3)$—, and more particularly a —CO—, —CH(OH)— or —$CH(NH_2)$— group, and preferentially a —CH(OH)— group.

Preferentially, a C-glycoside derivative of formula (I) is used, for which:
R denotes an unsubstituted linear $C_1$-$C_4$ and especially $C_1$-$C_2$ alkyl radical, in particular ethyl;

S represents a monosaccharide as described above; especially D-glucose, D-xylose, N-acetyl-D-glucosamine or L-fucose, in particular D-xylose;

X represents a group chosen from —CO—, —CH(OH)— and —CH(NH$_2$)— and preferentially a CH(OH)— group.

The salts that are acceptable for the non-therapeutic use of the compounds described in the present invention comprise conventional non-toxic salts of said compounds such as those formed from organic or inorganic acids. Examples that may be mentioned include the salts of mineral acids, such as sulfuric acid, hydrochloric acid, hydrobromic acid, hydriodic acid, phosphoric acid or boric acid. Mention may also be made of the salts of organic acids, which may comprise one or more carboxylic, sulfonic or phosphonic groups. They may be linear, branched or cyclic aliphatic acids or alternatively aromatic acids. These acids may also comprise one or more heteroatoms chosen from O and N, for example in the form of hydroxyl groups. Mention may be made especially of propionic acid, acetic acid, terephthalic acid, citric acid and tartaric acid.

When the compound of formula (I) comprises an acid group, neutralization of the acid group(s) may be performed with a mineral base, such as LiOH, NaOH, KOH, Ca(OH)$_2$, NH$_4$OH, Mg(OH)$_2$ or Zn(OH)$_2$; or with an organic base such as a primary, secondary or tertiary alkylamine, for example triethylamine or butylamine. This primary, secondary or tertiary alkylamine may comprise one or more nitrogen and/or oxygen atoms and may thus comprise, for example, one or more alcohol functions; mention may be made especially of amino-2-methyl-2-propanol, triethanolamine, dimethylamino-2-propanol or 2-amino-2-(hydroxymethyl)-1,3-propanediol. Mention may also be made of lysine or 3-(dimethylamino)propylamine.

The solvates that are acceptable for the compounds described in the present invention comprise conventional solvates such as those formed during the final step of preparation of said compounds due to the presence of solvents. Examples that may be mentioned include the solvates due to the presence of water or of linear or branched alcohols, for instance ethanol or isopropanol.

Among the C-glycoside derivatives of formula (I) used according to the invention, the ones that are most particularly considered are:

C-β-D-xylopyranoside-n-propane-2-one;
C-α-D-xylopyranoside-n-propane-2-one;
1-phenyl-2-(C-β-D-xylopyranoside)ethane-1-one;
1-phenyl-2-(C-α-D-xylopyranoside)ethane-1-one;
1-[2-(3-hydroxypropylamino)propyl]-C-β-D-xylopyranose;
1-[2-(3-hydroxypropylamino)propyl]-C-α-D-xylopyranose;
C-β-D-xylopyranoside-2-hydroxypropane;
C-α-D-xylopyranoside-2-hydroxypropane;
C-β-D-xylopyranoside-2-aminopropane;
C-α-D-xylopyranoside-2-aminopropane;
C-β-D-xylopyranoside-2-phenylaminopropane;
C-β-D-xylopyranoside-2-phenylaminopropane;
ethyl 3-methyl-4-(C-β-D-xylopyranoside)butyrate;
ethyl 3-methyl-4-(C-α-D-xylopyranoside)butyrate;
6-(C-β-D-xylopyranoside)-5-ketohexanoic acid;
6-(C-α-D-xylopyranoside)-5-ketohexanoic acid;
6-(C-β-D-xylopyranoside)-5-hydroxyhexanoic acid;
6-(C-α-D-xylopyranoside)-5-hydroxyhexanoic acid;
6-(C-β-D-xylopyranoside)-5-aminohexanoic acid;
6-(C-α-D-xylopyranoside)-5-aminohexanoic acid;
6-(C-β-D-xylopyranoside)-5-phenylaminohexanoic acid;
6-(C-α-D-xylopyranoside)-5-phenylaminohexanoic acid;
1-(C-β-D-xylopyranoside)hexane-2,6-diol;
1-(C-α-D-xylopyranoside)hexane-2,6-diol;
5-(C-β-D-xylopyranoside)-4-ketopentanoic acid;
5-(C-α-D-xylopyranoside)-4-ketopentanoic acid;
5-(C-β-D-xylopyranoside)-4-hydroxypentanoic acid;
5-(C-α-D-xylopyranoside)-4-hydroxypentanoic acid;
5-(C-β-D-xylopyranoside)-4-aminopentanoic acid;
5-(C-α-D-xylopyranoside)-4-aminopentanoic acid;
5-(C-β-D-xylopyranoside)-4-phenylaminopentanoic acid;
5-(C-α-D-xylopyranoside)-4-phenylaminopentanoic acid;
1-(C-β-D-xylopyranoside)pentane-2,5-diol;
1-(C-α-D-xylopyranoside)pentane-2,5-diol;
1-(C-β-D-fucopyranoside)propane-2-one;
1-(C-α-D-fucopyranoside)propane-2-one;
1-(C-β-D-fucopyranoside)propane-2-one;
1-(C-α-D-fucopyranoside)propane-2-one;
1-(C-β-D-fucopyranoside)-2-hydroxypropane;
1-(C-α-D-fucopyranoside)-2-hydroxypropane;
1-(C-β-L-fucopyranoside)-2-hydroxypropane;
1-(C-α-D-fucopyranoside)-2-hydroxypropane;
1-(C-β-D-fucopyranoside)-2-aminopropane;
1-(C-α-D-fucopyranoside)-2-aminopropane;
1-(C-β-L-fucopyranoside)-2-aminopropane;
1-(C-α-L-fucopyranoside)-2-aminopropane;
1-(C-β-D-fucopyranoside)-2-phenylaminopropane;
1-(C-α-D-fucopyranoside)-2-phenylaminopropane;
1-(C-β-L-fucopyranoside)-2-phenylaminopropane;
1-(C-α-L-fucopyranoside)-2-phenylaminopropane;
ethyl 3-methyl-4-(C-β-D-fucopyranoside)butyrate;
ethyl 3-methyl-4-(C-α-D-fucopyranoside)butyrate;
ethyl 3-methyl-4-(C-β-L-fucopyranoside)butyrate;
ethyl 3-methyl-4-(C-α-L-fucopyranoside)butyrate;
6-(C-β-D-fucopyranoside)-5-ketohexanoic acid;
6-(C-α-D-fucopyranoside)-5-ketohexanoic acid;
6-(C-β-L-fucopyranoside)-5-ketohexanoic acid;
6-(C-α-L-fucopyranoside)-5-ketohexanoic acid;
6-(C-β-D-fucopyranoside)-5-hydroxyhexanoic acid;
6-(C-α-D-fucopyranoside)-5-hydroxyhexanoic acid;
6-(C-β-L-fucopyranoside)-5-hydroxyhexanoic acid;
6-(C-α-L-fucopyranoside)-5-hydroxyhexanoic acid;
6-(C-β-D-fucopyranoside)-5-aminohexanoic acid;
6-(C-α-D-fucopyranoside)-5-aminohexanoic acid;
6-(C-β-L-fucopyranoside)-5-aminohexanoic acid;
6-(C-α-L-fucopyranoside)-5-aminohexanoic acid;
1-(C-β-D-fucopyranoside)hexane-2,6-diol;
1-(C-α-D-fucopyranoside)hexane-2,6-diol;
1-(C-β-L-fucopyranoside)hexane-2,6-diol;
1-(C-α-L-fucopyranoside)hexane-2,6-diol;
5-(C-β-D-fucopyranoside)-4-ketopentanoic acid;
5-(C-α-D-fucopyranoside)-4-ketopentanoic acid;
5-(C-β-L-fucopyranoside)hexane-2,6-diol)-4-ketopentanoic acid;
5-(C-α-L-fucopyranoside)hexane-2,6-diol)-4-ketopentanoic acid;
5-(C-β-D-fucopyranoside)-4-hydroxypentanoic acid;
5-(C-α-D-fucopyranoside)-4-hydroxypentanoic acid;
5-(C-β-L-fucopyranoside)-4-hydroxypentanoic acid;
5-(C-α-L-fucopyranoside)-4-hydroxypentanoic acid;
5-(C-β-D-fucopyranoside)-4-aminopentanoic acid;
5-(C-α-D-fucopyranoside)-4-aminopentanoic acid;
5-(C-β-L-fucopyranoside)-4-aminopentanoic acid;
5-(C-α-L-fucopyranoside)-4-aminopentanoic acid;
1-(C-β-D-fucopyranoside)pentane-2,5-diol;
1-(C-α-D-fucopyranoside)pentane-2,5-diol;
1-(C-β-L-fucopyranoside)pentane-2,5-diol;
1-(C-α-L-fucopyranoside)pentane-2,5-diol;
1-(C-β-D-glucopyranosyl)-2-hydroxylpropane;
1-(C-α-Glucopyranosyl)-2-hydroxylpropane;
1-(C-β-D-glucopyranosyl)-aminopropane;

1-(C-α-D-glucopyranosyl)-2-aminopropane;
1-(C-β-D-glucopyranosyl)-2-phenylaminopropane;
1-(C-α-D-glucopyranosyl)-2-phenylaminopropane;
ethyl 3-methyl-4-(C-β-D-glucopyranosyl)butyrate;
ethyl 3-methyl-4-(C-α-D-glucopyranosyl)butyrate;
6-(C-β-D-glucopyranosyl)-5-ketohexanoic acid;
6-(C-α-D-glucopyranosyl)-5-ketohexanoic acid;
6-(C-β-D-glucopyranosyl)-5-hydroxyhexanoic acid;
6-(C-α-D-glucopyranosyl)-5-hydroxyhexanoic acid;
6-(C-β-D-glucopyranosyl)-5-aminohexanoic acid;
6-(C-α-D-glucopyranosyl)-5-aminohexanoic acid;
6-(C-β-D-glucopyranosyl)-5-phenylaminohexanoic acid;
6-(C-α-D-glucopyranosyl)-5-phenylaminohexanoic acid;
1-(C-β-D-glucopyranosyl)hexane-2,6-diol;
1-(C-α-D-glucopyranosyl)hexane-2,6-diol;
6-(C-β-D-glucopyranosyl)-5-ketopentanoic acid;
6-(C-α-D-glucopyranosyl)-5-ketopentanoic acid;
6-(C-β-D-glucopyranosyl)-5-hydroxypentanoic acid;
6-(C-α-D-glucopyranosyl)-5-hydroxypentanoic acid;
6-(C-β-D-glucopyranosyl)-5-aminopentanoic acid;
6-(C-α-D-glucopyranosyl)-5-hydroxypentanoic acid;
6-(C-β-D-glucopyranosyl)-5-phenylaminopentanoic acid;
6-(C-α-D-glucopyranosyl)-5-phenylaminopentanoic acid;
1-(C-β-D-glucopyranosyl)pentane-2,6-diol;
1-(C-α-D-glucopyranosyl)pentane-2,6-diol;
1-(C-β-D-galactopyranosyl)-2-hydroxylpropane;
1-(C-α-D-galactopyranosyl)-2-hydroxylpropane;
1-(C-β-D-galactopyranosyl)-2-aminopropane;
1-(C-α-D-galactopyranosyl)-2-aminopropane;
1-(C-β-D-galactopyranosyl)-2-phenylaminopropane;
1-(C-α-D-galactopyranosyl)-2-phenylaminopropane;
ethyl 3-methyl-4-(β-D-galactopyranosyl)butyrate;
ethyl 3-methyl-4-(α-D-galactopyranosyl)butyrate;
6-(C-β-D-galactopyranosyl)-5-ketohexanoic acid;
6-(C-α-D-galactopyranosyl)-5-ketohexanoic acid;
6-(C-β-D-galactopyranosyl)-5-hydroxyhexanoic acid;
6-(C-α-D-galactopyranosyl)-5-hydroxyhexanoic acid;
6-(C-β-D-galactopyranosyl)-5-aminohexanoic acid;
6-(C-α-D-galactopyranosyl)-5-aminohexanoic acid;
6-(C-β-D-galactopyranosyl) 5-phenylaminohexanoic acid;
6-(C-α-D-galactopyranosyl) 5-phenylaminohexanoic acid;
1-(C-β-D-galactopyranosyl)hexane-2,6-diol;
1-(C-α-D-galactopyranosyl)hexane-2,6-diol;
6-(C-β-D-galactopyranosyl)-5-ketopentanoic acid;
6-(C-α-D-galactopyranosyl)-5-ketopentanoic acid;
6-(C-β-D-galactopyranosyl)-5-hydroxypentanoic acid;
6-(C-α-D-galactopyranosyl)-5-hydroxypentanoic acid;
6-(C-β-D-galactopyranosyl)-5-aminopentanoic acid;
6-(C-α-D-galactopyranosyl)-5-aminopentanoic acid;
6-(C-β-D-galactopyranosyl)-5-phenylaminopentanoic acid;
6-(C-α-D-galactopyranosyl)-5-phenylaminopentanoic acid;
1-(C-β-D-galactopyranosyl)pentane-2,6-diol;
1-(C-α-D-galactopyranosyl)pentane-2,6-diol;
1-(C-β-D-fucofuranosyl)propane-2-one;
1-(C-α-D-fucofuranosyl)propane-2-one;
1-(C-β-L-fucofuranosyl)propane-2-one;
1-(C-α-L-fucofuranosyl)propane-2-one;
3'-(acetamido-C-β-D-glucopyranosyl)propane-2'-one;
3'-(acetamido-C-α-D-glucopyranosyl)propane-2'-one;
1-(C-β-D-galactopyranosyl)-2-hydroxylpropane;
1-(C-α-D-galactopyranosyl)-2-aminopropane;
1-(acetamido-C-β-D-glucopyranosyl)-2-phenylaminopropane;
1-(acetamido-C-α-D-glucopyranosyl)-2-phenylaminopropane;
ethyl 3-methyl-4-(acetamido-C-β-D-glucopyranosyl) butyrate;
ethyl 3-methyl-4-(acetamido-C-α-D-glucopyranosyl) butyrate;
6-(acetamido-C-β-D-glucopyranosyl)-5-ketohexanoic acid;
6-(acetamido-C-α-D-glucopyranosyl)-5-ketohexanoic acid;
6-(acetamido-C-β-D-glucopyranosyl)-5-hydroxyhexanoic acid;
6-(acetamido-C-α-D-glucopyranosyl)-5-hydroxyhexanoic acid;
6-(acetamido-C-β-D-glucopyranosyl)-5-aminohexanoic acid;
6-(acetamido-C-α-D-glucopyranosyl)-5-aminohexanoic acid;
6-(acetamido-C-β-D-glucopyranosyl) 5-phenylaminohexanoic acid;
6-(acetamido-C-α-D-glucopyranosyl)-5-phenylaminohexanoic acid;
1-(acetamido-C-β-D-glucopyranosyl)hexane-2,6-diol;
1-(acetamido-C-α-D-glucopyranosyl)hexane-2,6-diol;
6-(acetamido-C-β-D-glucopyranosyl)-5-ketopentanoic acid;
6-(acetamido-C-α-D-glucopyranosyl)-5-ketopentanoic acid;
6-(acetamido-C-β-D-glucopyranosyl)-5-hydroxypentanoic acid;
6-(acetamido-C-α-D-glucopyranosyl)-5-hydroxy-pentanoic acid;
6-(acetamido-C-β-D-glucopyranosyl)-5-aminopentanoic acid;
6-(acetamido-C-α-D-glucopyranosyl)-5-aminopentanoic acid;
6-(acetamido-C-β-D-glucopyranosyl)-5-phenylamino-pentanoic acid;
6-(acetamido-C-α-D-glucopyranosyl)-5-phenylamino-pentanoic acid;
1-(acetamido-C-β-D-glucopyranosyl)pentane-2,6-diol;
1-(acetamido-C-α-D-glucopyranosyl)pentane-2,6-diol.

As non-limiting illustrations of C-glycoside derivatives that are more particularly suitable for use in the invention, mention may be made especially of the following derivatives: C-[β]-D-xylopyranoside-n-propane-2-one, C-[α]-D-xylopyranoside-n-propane-2-one, C-[β]-D-xylopyranoside-2-hydroxypropane, C-[α]-D-xylopyranoside-2-hydroxypropane, 1-(C-[β]-D-fucopyranoside)propane-2-one, 1-(C-[α]-D-fucopyranoside)propane-2-one, 1-(C-[β]-L-fucopyranoside)-propane-2-one, 1-(C-[α]L-fucopyranoside) propane-2-one, 1-(C-[β]-D-fucopyranoside)-2-hydroxypropane, 1-(C-[α]-D-fucopyranoside)-2-hydroxypropane, 1-(C-[β]-L-fucopyranoside)-2-hydroxypropane, 1-(C-[α]-L-fucopyranoside)-2-hydroxypropane, 1-(C-[β]-D-glucopyranosyl)-2-hydroxylpropane, 1-(C-[α]-D-glucopyranosyl)-2-hydroxylpropane, 1-(C-[β]-D-galactopyranosyl)-2-hydroxylpropane, 1-(C-[α]-D-galactopyranosyl)-2-hydroxylpropane, 1-(C-[β]-D-fucofuranosyl)propane-2-one, 1-(C-[α]-D-fucofuranosyl)propane-2~one, 1-(C-[β]-L-fucofuranosyl)propane-2-one, 1-(C-[α]-L-fucofuranosyl) propane-2-one, C-[β]-D-maltopyranoside-n-propane-2-one, C-[α]-D-maltopyranoside-n-propane-2-one, C-[β]-D-maltopyranoside-2-hydroxypropane, C-[α]-D-maltopyranoside-2-hydroxypropane, isomers thereof and mixtures thereof.

According to one embodiment, C-[β]-D-xylopyranoside-2-hydroxypropane or C-[α]-D-xylopyranoside-2-hydroxypropane, and better still C[β]-D-xylopyranoside-2-hydroxypropane, may be advantageously used for the preparation of a composition according to the invention.

According to one particular embodiment, the C-glycoside derivative may be C-[β]-D-xylopyranoside-2-hydroxypropane in the form of a solution containing 30% by weight of active material in a water/propylene glycol mixture (60/40% by weight), such as the product manufactured by Chimex under the trade name Mexoryl SBB®.

Needless to say, according to the invention, a C-glycoside derivative corresponding to formula (I) may be used alone or as a mixture with other C-glycoside derivatives and in all proportions. A C-glycoside derivative that is suitable for use in the invention may especially be obtained via the synthetic method described in document WO 02/051828.

The present invention also relates to the use of a composition according to the invention as defined previously, administered orally, topically or via cutaneous injection, especially for treating the skin and/or the scalp.

A composition in accordance with the invention as defined previously may especially be a cosmetic composition for haircare, in particular for stimulating hair growth, combating hair loss, slowing down hair loss or reinforcing the radiance of the hair.

Another object of the present invention is a treatment method, in particular a cosmetic or therapeutic method, for reducing or preventing the signs of aging of the skin or its integuments (hair, eyelashes, nails, etc.), by administering to an individual, preferably a human being, an effective amount of at least one monosaccharide as defined previously in combination with an effective amount of at least one additional compound as defined previously. An object of the invention is, in particular, a cosmetic process for treating wrinkled skin, in particular skin of the face and/or the forehead, comprising the topical application to the said skin of a composition comprising, in a physiologically acceptable medium, a combination of an effective amount of at least one monosaccharide as defined previously and an effective amount of at least one additional compound as defined previously.

The present invention also relates to the use of the composition or combination according to the invention, for reducing and/or preventing the signs of aging of the skin or its integuments.

The composition or combination according to the invention also makes it possible to stimulate the regeneration of epidermal and dermal cells, in the skin or the integuments, in particular keratinocytes and fibroblasts, especially by increasing their proliferation. This therefore provides a method, especially a cosmetic method, which is especially effective for combating the signs of chronological aging and/or photoaging.

The signs of photoaging correspond to internal degradation is of the skin due to exposure to ultraviolet radiation (actinic aging). The signs of chronological aging correspond to internal degradations of the skin due to the intrinsic aging of the individuals.

According to one preferred embodiment, the use according to the present invention is intended for improving the radiance of the complexion, for reducing and/or preventing the characteristics of wrinkles and/or fine lines, for improving and/or reducing the microrelief of the skin, for making the skin smooth and/or for improving the mechanical properties of the skin and/or for increasing the resistance of the skin to mechanical attack, such as rubbing, tensions or frictions and/or for promoting skin repair.

According to another aspect of the invention, the use of the composition or of the combination according to the invention makes it possible to improve the density of the skin, its firmness and/or the cohesion of its various compartments, in particular the cohesion of the dermis with the epidermis.

The present invention also relates to the use of the composition or combination according to the invention for preventively or curatively treating wrinkles and/or fine lines, withered skin, lack of skin elasticity and/or tonicity, thinning of the dermis, degradation of collagen fibres, flaccid skin, thinned skin and/or any internal degradation of the skin caused by exposure to ultraviolet radiation.

The composition or combination according to the invention makes it possible to stimulate the synthesis of glycosaminoglycans containing a D-glucosamine and/or N-acetyl-D-glucosamine residue, advantageously hyaluronic acid, and/or proteoglycans, advantageously proteoglycans containing hyaluronic acid, by the fibroblasts and/or keratinocytes.

The composition or combination according to the invention also has the effect of increasing the synthesis of laminins, preferably laminin V, and the synthesis of collagens, preferably chosen from procollagen I, collagen IV and collagen VII.

The amount of the active ingredients, chosen from the monosaccharides and C-glycosides and derivatives defined previously, to be used according to the invention depends on the desired cosmetic or therapeutic effect, and may thus vary within a wide range. A person skilled in the art can thus readily, on the basis of his general knowledge, determine the appropriate amounts.

Thus, and according to one preferred embodiment, the composition according to the invention comprises at least one monosaccharide as defined above in an amount of between 0.001% and 30% by weight relative to the total weight of the composition, in particular between 0.1% and 10% by weight and more particularly between 0.5% and 6% by weight relative to the total weight of the composition.

According to one preferred embodiment, the composition according to the invention comprises a C-glycoside and/or at least one derivatives thereof in an amount of between 0.001% and 30% by weight relative to the total weight of the composition, in particular between 0.1% and 10% by weight and more particularly between 0.5% and 6% by weight relative to the total weight of the composition.

In particular, the composition according to the invention does not comprise a combination of xylitol and mannitol.

In particular, the composition according to the invention does not comprise a tensioning agent.

In general, the term "tensioning agent" generally means any polymer that is soluble or dispersible in water at a temperature ranging from 25° C. to 50° C. at a concentration of 7% by weight in water or at the maximum concentration at which a medium of uniform appearance is formed and producing at this concentration of 7% or at this maximum concentration in water a shrinkage of more than 15% in the test described below.

The maximum concentration at which a medium of uniform appearance forms is determined to within ±20% and preferably to within ±5%.

The expression "medium of uniform appearance" means a medium that does not contain any aggregates that are visible to the naked eye.

For the determination of the said maximum concentration, the tensioning agent is gradually added to the water with deflocculating stirring at a temperature ranging from 25° C. to 50° C., and the mixture is then stirred for one hour. The mixture thus prepared is then examined after 24 hours to see if it is of uniform appearance (absence of aggregates visible to the naked eye).

The tensioning effect may be characterized by an in vitro shrinkage test.

A homogeneous mixture of the tensioning agent in water, at a concentration of 7% by weight or at the maximum concentration defined above, is prepared beforehand and as described previously.

30 µl of the homogeneous mixture are placed on a rectangular sample (10×40 mm, thus having an initial width $L_0$ of 10 mm) of elastomer with a modulus of elasticity of 20 MPa and a thickness of 100 µm.

After drying for 3 hours at 22±3° C. and 40±10% relative humidity RH, the elastomer sample has a shrunken width, noted $L_{3h}$, due to the tension exerted by the applied tensioning agent.

The tensioning effect (TE) of the said polymer is then quantified in the following manner:

'TE'=$(L_0-L_{3h}/L_0)\times 100$ as % with $L_0$=initial width 10 mm and
$L_{3h}$=width after 3 hours of drying
The tensioning agent may be chosen from:
a) plant or animal proteins and hydrolysates thereof;
b) polysaccharides of natural origin;
c) mixed silicates;
d) colloidal particles of mineral fillers;
e) synthetic polymers;
and mixtures thereof.

A person skilled in the art will know how to choose, from the chemical categories listed above, the materials corresponding to the test as described previously.

The composition according to the invention is suitable for topical administration to the skin or its integuments, oral administration or cutaneous injection, in particular in the form of a sterile solution.

Preferably, the topical administrations according to the invention are in the form of a cream, a gel, a lotion, a milk, an oil, an ointment, a wax, a mousse, a paste, a serum, a pomade or a shampoo.

Preferably also, the oral administrations according to the invention are in the form of a gel capsules, a tablet or pills.

The monosaccharide according to the invention, and the C-glycoside or derivatives thereof, are more particularly present in the composition according to the invention as active agent (or active ingredient), in particular as sole active agents.

According to the invention, the terms "active agent" and "active ingredient" more specifically mean a compound which, when administered to an individual, in particular to a human being, plays a direct biological role on the body, in particular on the skin or its integuments, in particular without improving the biological or mechanical effect of another compound present in the composition according to the invention.

In general, the medium in which the active principles of the composition as defined previously are included is a physiologically acceptable medium, in particular a cosmetically or pharmaceutically acceptable medium, and may be anhydrous or aqueous. It may thus comprise an aqueous phase and/or a fatty phase.

The physiologically acceptable medium in which the compounds according to the invention may be employed, and also the constituents thereof, their amount, the galenical form of the composition, its mode of preparation and its mode of administration, may be chosen by a person skilled in the art on the basis of his general knowledge, as a function of the desired type of composition.

When the composition is a composition intended for topical administration, it may advantageously be in the form of aqueous or aqueous-alcoholic solutions, oil-in-water (O/W) or water-in-oil (W/O) emulsions or multiple emulsions (triple: W/O/W or O/W/O), nanoemulsions, in particular O/W nanoemulsions, in which the size of the drops is less than 100 nm, aqueous gels, or dispersions of a fatty phase in an aqueous phase with the aid of spherules, these spherules possibly being polymer nanoparticles such as nanospheres and nanocapsules or lipid vesicles of ionic and/or nonionic type (liposomes, niosomes or oleosomes (as described in patent applications FR 2 709 666 and FR 2 725 369)).

These compositions are prepared according to the usual methods.

In addition, the compositions that may be used according to the invention may be more or less fluid and may have the appearance of a white or coloured cream, a pomade, a milk, a lotion, a serum, a paste or a mousse. They may optionally be applied to the skin in aerosol form. They may also be in solid form, for example in stick form.

For local application to the hair or the scalp, the composition may be in the form of aqueous, alcoholic or aqueous-alcoholic solutions; in the form of creams, gels, emulsions or mousses; in the form of aerosol compositions also comprising a propellant under pressure.

When the composition is in aqueous form, especially in the form of an aqueous dispersion, emulsion or solution, it may comprise an aqueous phase, which may comprise water, a floral water and/or a mineral water.

When the composition is an emulsion, the proportion of the fatty phase may range from about 5% to 80% by weight and preferably from about 2% to 50% by weight relative to the total weight of the composition. The oils, waxes, emulsifiers and co-emulsifiers used in the composition in emulsion form are chosen from those conventionally used in cosmetics. The emulsifier and the co-emulsifier are present in the composition in a proportion ranging from 0.3% to 30% by weight and preferably from 0.5% to 20% by weight relative to the total weight of the composition. The emulsion may also contain lipid vesicles.

When the composition is an oily solution or gel, the fatty phase may represent more than 90% of the total weight of the composition.

The oily phase may also comprise any common liposoluble or lipodispersible additive, as indicated hereinbelow.

It may especially comprise fatty substances such as waxes, pasty compounds, fatty alcohols or fatty acids. The oily phase contains at least one oil, more particularly at least one cosmetic oil. The term "oil" means a fatty substance that is liquid at room temperature (25° C.).

As oils that may be used in the composition of the invention, examples that may be mentioned include:
hydrocarbon-based oils of animal origin, such as perhydrosqualene;
hydrocarbon-based oils of plant origin, such as liquid triglycerides of fatty acids containing from 4 to 10 carbon atoms, for instance heptanoic or octanoic acid triglycerides, or alternatively, for example, sunflower oil, corn oil, soybean oil, marrow oil, grapeseed oil, sesameseed oil, hazelnut oil, apricot oil, macadamia oil, arara oil, coriander oil, castor oil, avocado oil, caprylic/capric acid triglycerides, for instance those sold by the company Stearineries Dubois or those sold under the names Miglyol 810, 812 and 818 by the company Dynamit Nobel, jojoba oil, shea butter oil and caprylyl glycol;
synthetic esters and ethers, especially of fatty acids, for instance the oils of formulae $R^1COOR^2$ and $R^1OR^2$ in which $R^1$ represents a fatty acid or a fatty alcohol residue containing from 8 to 29 carbon atoms and $R^2$ represents a branched or unbranched hydrocarbon-based chain containing from 3 to 30 carbon atoms, for instance Purcellin oil, 2-octyldodecyl stearate, 2-octyldodecyl erucate, isostearyl isostearate; hydroxylated esters, for instance isostearyl lactate, octyl hydroxystearate, octyldodecyl hydroxystearate, diisostearyl malate or triisocetyl citrate; fatty alcohol heptanoates, octanoates or decanoates; polyol esters, for instance propylene glycol dioctanoate, neopentyl glycol diheptanoate and diethylene glycol diisononanoate; and pentaerythritol esters, for instance pentaerythrityl tetraisostearate, or isopropyl lauroyl sarcosinate, sold especially under the trade name Eldew SL 205 by the company Ajinomoto;

linear or branched hydrocarbons, of mineral or synthetic origin, such as volatile or non-volatile liquid paraffins, and derivatives thereof, petroleum jelly, polydecenes, isohexadecane, isododecane, hydrogenated polyisobutene such as Parleam oil, or the mixture of n-undecane (C11) and of n-tridecane (C13) sold under the reference Cetiol UT by the company Cognis;

fluoro oils that are partially hydrocarbon-based and/or silicone-based, for instance those described in document JP-A-2 295 912;

silicone oils, for instance volatile or non-volatile polymethylsiloxanes (PDMS) with a linear or cyclic silicone chain, which are liquid or pasty at room temperature, in particular volatile silicone oils, especially cyclopolydimethylsiloxanes (cyclomethicones) such as cyclohexadimethylsiloxane and cyclopentadimethylsiloxane; polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes;

mixtures thereof.

In the list of oils mentioned above, the term "hydrocarbon-based oil" means any oil mainly comprising carbon and hydrogen atoms, and possibly ester, ether, fluoro, carboxylic acid and/or alcohol groups.

The other fatty substances that may be present in the oily phase are, for example, fatty acids containing from 8 to 30 carbon atoms, for instance stearic acid, lauric acid, palmitic acid and oleic acid; waxes, for instance lanolin wax, beeswax, carnauba wax or candelilla wax, paraffin wax, lignite wax or microcrystalline waxes, ceresin or ozokerite, and synthetic waxes, for instance polyethylene waxes and Fischer-Tropsch waxes; silicone resins such as trifluoromethyl-C1-4-alkyl dimethicone and trifluoropropyl dimethicone; and silicone elastomers, for instance the products sold under the name KSG by the company Shin-Etsu, under the name Trefil, BY29 or EPSX by the company Dow Corning, or under the name Gransil by the company Grant Industries.

These fatty substances may be chosen in a varied manner by a person skilled in the art so as to prepare a composition having the desired properties, for example in terms of consistency or texture.

The emulsions generally contain at least one emulsifier chosen from amphoteric, anionic, cationic and nonionic emulsifiers, used alone or as a mixture, and optionally a co-emulsifier. The emulsifiers are chosen in an appropriate manner according to the emulsion to be obtained (W/O or O/W). The emulsifier and the co-emulsifier are generally present in the composition in a proportion ranging from 0.3% to 30% by weight and preferably from 0.5% to 20% by weight relative to the total weight of the composition.

For W/O emulsions, examples of emulsifiers that may be mentioned include dimethicone copolyols, such as the mixture of cyclomethicone and dimethicone copolyol sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM 90® by the company Goldschmidt. A crosslinked elastomeric solid organopolysiloxane comprising at least one oxyalkylene group, such as those obtained according to the procedure of Examples 3, 4 and 8 of U.S. Pat. No. 5,412,004 and of the examples of U.S. Pat. No. 5,811,487, especially the product of Example 3 (synthesis example) of U.S. Pat. No. 5,412,004, such as the product sold under the reference KSG 21 by the company Shin-Etsu, may also be used as surfactants for W/O emulsions.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof, such as the mixture of glyceryl stearate and PEG-40 stearate.

These compositions may also be O/W emulsions stabilized with particles, for instance the polymer particles described in patent FR 2 760 641, or crosslinked or non-crosslinked amphiphilic polymers, as described in patent applications FR 2 853 543 and FR 2 819 175.

In a known manner, the cosmetic composition may also contain adjuvants that are common in cosmetics, such as hydrophilic or lipophilic gelling agents, hydrophilic or lipophilic active agents, preserving agents, antioxidants, solvents, fragrances, fillers, odour absorbers and dyestuffs. The amounts of these various adjuvants are those conventionally used in the cosmetics field, and range, for example, from about 0.01% to 10% of the total weight of the composition. Depending on their nature, these adjuvants may be introduced into the fatty phase, into the aqueous phase and/or into lipid spherules.

As solvents that may be used in the invention, mention may be made of lower alcohols, for instance ethanol, isopropanol, dipropylene glycol, butylene glycol and propylene glycol.

As hydrophilic gelling agents that may be used in the invention, non-limiting examples that may be mentioned include carboxyvinyl polymers (Carbomer®), acrylic copolymers such as acrylate/alkylacrylate copolymers, polyacrylamides, polysaccharides such as hydroxypropylcellulose, natural gums and clays, and lipophilic gelling agents that may be mentioned include modified clays such as bentones, metal salts of fatty acids, for instance aluminium stearates, hydrophobic silica, ethylcellulose and polyethylene.

When the composition is administered orally, it is advantageously in the form of a gel capsule, a tablet or pills. When the composition is administered via cutaneous injection, it is in particular in the form of a sterile solution.

The compositions of the invention may contain other hydrophilic or lipophilic active agents. These active agents are chosen especially from antioxidants, dermo-relaxing or dermo-decontracting agents, anti-aging agents, anti-glycation agents, agents for stimulating the synthesis of dermal or epidermal macromolecules and/or for preventing their degradation, agents for stimulating fibroblast or keratinocyte proliferation and/or keratinocyte differentiation, agents for promoting maturation of the horny envelope, NO-synthase inhibitors, and agents for stimulating the energy metabolism of cells. Lists of these active agents are given hereinbelow as illustrations, and should not in any way be considered as limiting.

Anti-Aging Agents:

Among the active agents that are known for combating the signs of aging, especially aging of the skin, mention may be made especially of:

vitamin B3, coenzyme Q10 (or ubiquinone), vitamin B9, vitamin E, vitamin E derivatives, such as the phosphate derivative, for instance TPNA® sold by the company Showa Denko, resveratrol or derivatives thereof, for instance Resveratrate® sold by the company Estée Lauder, retinol or derivatives thereof, and a mixture thereof.

Anti-Glycation Agents:

The term "anti-glycation agent" means a compound that prevents and/or reduces the glycation of skin proteins, in particular dermal proteins such as collagen.

Anti-glycation agents that may especially be mentioned include extracts of plants of the Ericacea family, such as an extract of blueberry (*Vaccinium angustifolium* or *Vaccinium myrtillus*), for example the product sold under the name Blueberry Herbasol Extract PG by the company Cosmetochem, ergothioneine and derivatives thereof, hydroxystilbenes and derivatives thereof, such as resveratrol and 3,3',5,5'-tetrahydroxystilbene (these anti-glycation agents are described in patent applications FR 2 802 425, FR 2 810 548, FR 2 796 278 and FR 2 802 420, respectively), dihydroxystilbenes and derivatives thereof, polypeptides of arginine and of lysine such as the product sold under the name Amadorine® by the company Solabia, carcinine hydrochloride (sold by Exsymol under the name Alistin®), an extract of *Helianthus annuus*, for instance Antiglyskin® from Silab, wine extracts such as the extract of powdered white wine on a maltodextrin support sold under the name Vin blanc déshydraté 2F by the company Givaudan, thioctic acid (or alpha-lipoic acid), a mixture of extract of bearberry and of marine glycogen, for instance Aglycal LS 8777® from Laboratoires Sérobiologiques, and an extract of black tea, for instance Kombuchka® from Sederma, and mixtures thereof.

Preferred anti-glycation agents that will be mentioned include extracts of blueberry (*Vaccinium myrtillus*) and extracts of black tea.

Agents for Stimulating the Synthesis of Dermal and/or Epidermal Macromolecules and/or for Preventing their Degradation Among the active agents for stimulating the dermal macromolecules or for preventing their degradation, mention may be made of those acting:

either on collagen synthesis, such as extracts of *Centella asiatica*, asiaticosides and derivatives thereof; synthetic peptides such as iamin, biopeptide CL or palmitoyl oligopeptide sold by the company Sederma; peptides extracted from plants, such as the soybean hydrolysate sold by the company Coletica under the trade name Phytokine®; rice peptides such as Nutripeptide® from Silab, methylsilanol mannuronate such as Algisium C® is sold by Exsymol; plant hormones such as auxins and lignans; folic acid; and an extract of *Medicago sativa* (alfalfa) such as the product sold by Silab under the name Vitanol®; a peptide extract of hazelnut such as the product sold by Solabia under the name Nuteline C®; and arginine;

or on the inhibition of collagen degradation, in particular agents acting on the inhibition of metalloproteases (MMP) more particularly such as MMP 1, 2, 3 and 9. Mention may be made of: retinoids and derivatives, extracts of *Medicago sativa* such as Vitanol® from Silab, an extract of *Aphanizomenon flos-aquae* (Cyanophyceae) sold under the name Lanablue® by Atrium Biotechnologies, oligopeptides and lipopeptides, lipoamino acids, the malt extract sold by the company Coletica under the trade name Collalift®; blueberry or rosemary extracts; lycopene; isoflavones, derivatives thereof or plant extracts containing them, in particular extracts of soybean (sold, for example, by the company Ichimaru Pharcos under the trade name Flavosterone SB®), of red clover, of flax or of kakkon; an extract of lychee; Dipalmitoyl Hydroxyproline sold by SEPPIC under the name Sepilift DPHP®: *Baccharis genistelloides* or Baccharine sold by Silab, an extract of moringa such as Arganyl LS 9781® from Cognis; the sage extract described in patent application FR-A-2 812 544 from the Labiatae family (*Salvia officinalis* from the company Flacksmann), an extract of rhododendron, a blueberry extract, and an extract of *Vaccinium myrtillus* such as those described in patent application FR-A-2 814 950;

or on the synthesis of molecules belonging to the elastin family (elastin and fibrillin), such as: retinol and derivatives, in particular retinyl palmitate; the extract of *Saccharomyces cerevisiae* sold by the company LSN under the trade name Cytovitin®; and the extract of the alga *Macrocystis pyrifera* sold by the company Secma under the trade name Kelpadelie®; a peptide extract of hazelnut such as the product sold by the company Solabia under the trade name Nuteline C®;

or on inhibition of elastin degradation, such as the peptide extract of seeds of *Pisum sativum* sold by the company LSN under the trade name Parelastyl®; heparinoids; and the N-acylamino amide compounds described in patent application WO 01/94381, such as {2-[acetyl(3-trifluoromethylphenyl)amino]-3-methylbutyrylamino}acetic acid, also known as N—[N-acetyl, N'-(3-trifluoromethyl)phenylvalyl]glycine, or N-acetyl-N-[3-(trifluoromethyl)phenyl]valylglycine or acetyl trifluoromethylphenylvalylglycine, or an ester thereof with a $C_1$-$C_6$ alcohol; an extract of rice peptides such as Colhibin® from Pentapharm, or an extract of *Phyllanthus emblica* such as Emblica® from Rona;

or on the synthesis of glycosaminoglycans, such as the product of fermentation of milk with *Lactobacillus vulgaris*, sold by the company Brooks under the trade name Biomin Yoghurt®; the extract of the brown alga *Padina pavonica* sold by the company Alban Müller under the trade name HSP3®; the *Saccharomyces cerevisiae* extract available especially from the company Silab under the trade name Firmalift® or from the company LSN under the trade name Cytovitin®; an extract of *Laminaria ochroleuca* such as Laminaine® from Secma; essence of Mamaku from Lucas Meyer, and an extract of Cress (Odraline® from Silab);

or on the synthesis of fibronectin, such as the extract of the zooplankton Salina sold by the company Seporga under the trade name GP4G®; the yeast extract available especially from the company Alban Müller under the trade name Drieline®; and the palmitoyl pentapeptide sold by the company Sederma under the trade name Matrixyl®.

Among the active agents for stimulating epidermal macromolecules, such as fillagrin and keratins, mention may be made especially of the extract of lupin sold by the company Silab under the trade name Structurine®; the extract of *Fagus sylvatica* beech buds sold by the company Gattefosse under the trade name Gatuline® RC; and the extract of the zooplankton Salina sold by the company Seporga under the trade name GP4G®; the copper tripeptide from Procyte; a peptide extract of *Voandzeia substerranea* such as the product sold by the company Laboratoires Sérobiologiques under the trade name Filladyn LS 9397®.

Preferably, an active agent that stimulates the synthesis of dermal and/or epidermal macromolecules and/or that prevents their degradation, chosen from agents for stimulating the synthesis of glycosaminoglycans, agents for inhibiting elastin degradation, agents for stimulating fibronectin synthesis, agents for stimulating the synthesis of epidermal macromolecules, and mixtures thereof, will be used.

Even more preferentially, an active agent that stimulates the synthesis of the glycosaminoglycans, chosen from an extract of the brown alga *Padina pavonica*, an extract of *Saccharomyces cerevisiae*, an extract of *Laminaria ochroleuca*, essence of Mamaku, and an extract of cress, and mixtures thereof, will be used.

As preferred active agents for stimulating the synthesis of dermal and/or epidermal macromolecules and/or for preventing their degradation, mention may be made of:

synthetic peptides such as iamin, the biopeptide CL or palmitoyloligopeptide sold by the company Sederma; peptides extracted from plants, such as the soybean hydrolysate sold by the company Coletica under the trade name Phytokine®; rice peptides such as Nutripeptide® from Silab, methylsilanol mannuronate such as Algisium C® sold by Exsymol; folic acid; an extract of *Medicago sativa* (alfalfa), such as the product sold by Silab under the name Vitanol®; a peptide extract of hazelnut, such as the product sold by the company Solabia under the name Nuteline C®; arginine; an extract of *Aphanizomenon flos-aquae* (Cyanophyceae) sold under the name Lanablue® by Atrium Biotechnologies, the malt extract sold by the company Coletica under the trade name Collalift®, lycopene; an extract of lychee; an extract of moringa such as Arganyl LS 9781® from Cognis; an extract of *Vaccinium myrtillus* such as those described in patent application FR-A-2 814 950; retinol and derivatives thereof, in particular retinyl palmitate; the extract of *Saccharomyces cerevisiae* sold by the company LSN under the trade name Cytovitin®; a peptide extract of hazelnut such as the product sold by the company Solabia under the name Nuteline C®; {2-[acetyl(3-trifluoromethylphenyl)amino]-3-methylbutyrylamino}acetic acid, also known as N—[N-acetyl, N'-(3-trifluoromethyl)phenylvalyl]glycine, or N-acetyl-N-[3-(trifluoromethyl)phenyl]valylglycine or acetyl trifluoromethylphenylvalylglycine, or an ester thereof with a $C_1$-$C_6$ alcohol; an extract of rice peptides such as Colhibin® from Pentapharm, or an extract of *Phyllanthus emblica* such as Emblica® from Rona; the extract of the brown alga *Padina pavonica* sold by the company Alban Müller under the trade name HSP3®; the extract of *Saccharomyces cerevisiae* available especially from the company Silab under the trade name Firmalift® or from the company LSN under the trade name Cytovitin®; an extract of *Laminaria ochroleuca* such as Laminaine® from Secma; the essence of Mamaku from Lucas Meyer, the extract of lupin sold by the company Silab under the trade name Structurine®; the extract of *Fagus sylvatica* beech buds sold by the company Gattefosse under the trade name Gatuline® RC.

Agents for Stimulating Fibroblast or Keratinocyte Proliferation and/or Keratinocyte Differentiation The agents for stimulating fibroblast proliferation that may be used in the composition according to the invention may be chosen, for example, from plant proteins or polypeptides, extracted especially from soybean (for example a soybean extract sold by the company LSN under the name Eleseryl SH-VEG 8® or sold by the company Silab under the trade name Raffermine®); an extract of hydrolysed soybean proteins such as Ridulisse® from Silab; and plant hormones such as gibberellins and cytokinins; a peptide extract of hazelnut such as the product sold by the company Solabia under the name Nuteline C®.

Preferably, an agent that promotes keratinocyte proliferation and/or differentiation will be used.

The agents for stimulating keratinocyte proliferation that may be used in the composition according to the invention especially comprise phloroglucinol, the extract of *Hydrangea macrophylla* leaves, for instance Amacha Liquid E® from Ichimaru Pharcos, a yeast extract such as Stimoderm® from CLR; the extract of *Larrea divaricata* such as Capislow® from Sederma, mixtures of extract of papaya, of olive leaves and of lemon, such as Xyleine® from Vincience, retinol and esters thereof, including retinyl palmitate, the nut cake extracts sold by the Gattefosse and the extracts of *Solanum tuberosum* such as Dermolectine® sold by Sederma.

Among the agents for stimulating keratinocyte differentiation are, for example, minerals such as calcium; a peptide extract of lupin, such as the product sold by the company Silab under the trade name Structurine®; sodium beta-sitosteryl sulfate, such as the product sold by the company Seporga under the trade name Phytocohesine®; and a water-soluble extract of corn, such as the product sold by the company Solabia under the trade name Phytovityl®; a peptide extract of *Voandzeia substerranea* such as the product sold by the company Laboratoires Sérobiologiques under the trade name Filladyn LS 9397®; and lignans such as secoisolariciresinol, and retinol and esters thereof, including retinyl palmitate.

As agents for stimulating keratinocyte proliferation and/or differentiation, mention may also be made of oestrogens such as oestradiol and homologues; cytokines.

As preferred active agents for stimulating fibroblast or keratinocyte proliferation and/or keratinocyte differentiation, mention will be made of plant proteins or polypeptides, extracted especially from soybean (for example a soybean extract sold by the company LSN under the name Eleseryl SH-VEG 8® or sold by the company Silab under the trade name Raffermine®); an extract of hydrolysed soybean proteins such as Ridulisse® from Silab; a peptide extract of hazelnut such as the product sold by the company Solabia under the name Nuteline C®; adenosine, phloroglucinol, a yeast extract such as Stimoderm® from CLR; a peptide extract of lupin such as the product sold by the company Silab under the trade name Structurine®; a water-soluble corn extract, such as the product sold by the company Solabia under the trade name Phytovityl®; a peptide extract of *Voandzeia substerranea*, such as the product sold by the company Laboratoires Sérobiologiques under the trade name Filladyn LS 9397®; retinol and esters thereof, including retinyl palmitate.

Agents for Promoting the Maturation of the Horny Envelope

Agents that participate in the maturation of the horny envelope, which becomes impaired with age and induces a decrease in transglutaminase activity, may be used in the compositions of the invention. Examples that may be mentioned include urea and derivatives thereof and in particular Hydrovance® from National Starch and the other active agents mentioned in L'Oréal patent application FR 2 877 220.

NO-Synthase Inhibitors

The agent with an inhibitory action on NO synthase may be chosen from OPCs (procyannidol oligomers); plant extracts of the species *Vitis vinifera* sold especially by the company Euromed under the name "Leucocyanidines de raisins extra", or by the company Indena under the name Leucoselect®, or finally by the company Hansen under the name "Extrait de marc de raisin"; plant extracts of the species *Olea europaea* preferably obtained from olive tree leaves and sold especially by the company Vinyals in the form of a dry extract, or by the company Biologia & Technologia under the trade name Eurol® BT; and plant extracts of the species *Gingko biloba*, preferably a dry aqueous extract of this plant sold by the company Beaufour under the trade name "*Ginkgo biloba* extrait standard", and mixtures thereof.

Agents for Stimulating the Energy Metabolism of Cells

The active agent for stimulating the energy metabolism of cells may be chosen, for example, from biotin, an extract of *Saccharomyces cerevisiae* such as Phosphovital® from Sederma, the mixture of sodium, manganese, zinc and magnesium salts of pyrrolidonecarboxylic acid, for instance Physiogenyl® from Solabia, a mixture of zinc, copper and magnesium gluconate, such as Sepitonic M3® from SEPPIC, and mixtures thereof; and a beta-glucan derived from *Saccharomyces cerevisiae*, such as the product sold by the company Mibelle AG Biochemistry.

The invention also relates to a cosmetic process for treating the skin, for reducing or preventing the signs of aging of the skin or its integuments (hair, eyelashes, nails, etc.), comprising at least one step that consists in applying to the skin at least one composition as defined previously.

The process according to the invention more specifically comprises at least one step that consists in applying at least one composition as defined previously to the skin of individuals whose skin present at least one of the signs of cutaneous aging recalled previously.

More particularly, it comprises at least one step that consists in applying at least one composition as defined previously to the skin of individuals with skin or an area of skin that is aged, wrinkles, soft and/or flaccid or two areas of the body showing loss of elasticity and/or firmness and/or tonicity.

The composition according to the invention may be applied to the part of the skin or integuments to be treated, in particular to the face, the body, the neck, the hands, the hair or the scalp, preferably daily or several times a day. The application may, for example, be repeated every day over a variable period according to the desired effects, generally from 3 to 6 weeks, but may be prolonged or pursued continuously.

According to one alternative, the composition according to the invention may be administered by injection optionally in combination with filling products. Specifically, one of the solutions adopted for combating wrinkles and/or the loss of volume of soft tissue is the use of filling products (or filler). This filling may be achieved by using non-resorbable products, such as polyacrylamide gels or polymethyl methacrylate (PMMA) particles. However, these compounds may lead to intolerance reactions of the type such as inflammation or hypersensitivity.

The use of resorbable components, such as proteins, fats, collagen or hyaluronic acid, is preferred. However, these compounds are degraded relatively quickly in the body, which reduces their efficacy. To overcome this, more or less expensive crosslinking of these components must be performed. At the present time, the hyaluronic acid used in pharmaceutical forms or medical devices is in the form of a sodium hyaluronate gel. The monosaccharide according to the invention or the compositions containing it may also be applied by mesotherapy. Mesotherapy is a technique of treatment via intraepidermal and/or intradermal and/or subcutaneous injection of active product(s), for instance micronutrients, vitamins and/or hyaluronic acid. The compositions are administered according to this technique via injection in the form of multiple small droplets into the epidermis, the dermo-epidermal junction and/or the dermis in order especially to perform subcutaneous layering. The mesotherapy technique is especially described in the publication "Traité de mésothérapie" by Jacques Le Coz, published by Masson, 2004. Mesotherapy performed on the face is also referred to as a mesolift or a mesoglow.

Thus, another object of the present invention may be a device, in particular a medical device, comprising an effective amount of at least one monosaccharide as defined previously, in combination with an effective amount of at least one C-glycoside or a derivative thereof. This device may be suitable for intraepidermal and/or intradermal and/or subcutaneous injection. The combination of active agents as defined above is dissolved in a sterile medium. The said device may comprise at least one other compound, for instance at least one resorbable or non-resorbable product, such as those mentioned above, which is optionally crosslinked.

The said device may be, for example, a syringe with a needle or an injection device without a needle, such as those used in the care technique known as mesotherapy. A kit comprising a device may also be envisaged, the said kit comprising a device, in particular a syringe or an injection device, and at least a combination of active agents, monosaccharide(s) and C-glycoside derivative(s), as defined above. The said kit may also comprise a needle. The said device may be in ready-to-use form, i.e. prefilled, or may need to be filled before use. In the latter case, a composition or another device (such as a vial) comprises the said combination of active agents, monosaccharide(s) and C-glycoside or derivative(s), optionally in combination with at least one other active compound, for instance at least one resorbable or non-resorbable product, such as the filling products mentioned above, which is optionally crosslinked.

The injection of the combination according to the invention may be performed simultaneously with, or before or after, the application to the skin or the integuments of another cosmetic or pharmaceutical composition, preferably a dermatological composition, comprising, in a physiologically acceptable support, at least one other active agents, as mentioned above.

According to another aspect, the invention also relates to a cosmetic assembly comprising: i) a container delimiting at least one compartment, the said container being closed by a closing member; and ii) a composition as defined previously, placed inside the said compartment.

The container may be in any suitable form. It may especially be in the form of a bottle, a tube, a jar, a case, a can, a sachet or a box. The closing member may be in the form of a removable stopper, a lid, a cover, a tear-off strip or a cap, especially of the type comprising a body fixed to the container and a cap articulated on the body. It may also be in the form of a member ensuring the selective closure of the container, especially a pump, a valve or a clapper.

The container may be combined with an applicator. The applicator may be in the form of a fine brush, as described, for example, in patent FR 2 722 380. The product may be contained directly in the container, or indirectly. By way of example, the composition may be arranged on an impregnated support, especially in the form of a wipe or a pad, and arranged (individually or in plurality) in a box or in a sachet. Such a support incorporating the product is described, for example, in patent application WO 01/03538.

The closing member may be coupled to the container by screwing.

Alternatively, the coupling between the closing member and the container is done other than by screwing, especially via a bayonet mechanism, by click-fastening, gripping, welding, bonding or by magnetic attraction. The term "click-fastening" in particular means any system involving the crossing of a bead or cord of material by elastic deformation of a portion, especially of the closing member, followed by return to the elastically unconstrained position of the said portion after the crossing of the bead or cord.

The container may be at least partially made of thermoplastic material. Examples of thermoplastic materials that may be mentioned include polypropylene or polyethylene.

Alternatively, the container is made of non-thermoplastic material, especially glass or metal (or alloy).

The container may have rigid or deformable walls, especially in the form of a tube or a tube or bottle. The container may comprise means for initiating or facilitating the distribution of the composition. By way of example, the container may have deformable walls so as to allow the composition to exit in response to a positive pressure inside the container, this positive pressure being caused by elastic (or non-elastic) squeezing of the walls of the container.

The contents of the patents or patent applications mentioned previously are incorporated by reference into the present patent application.

According to one particular mode, the invention relates to a cosmetic assembly comprising:

a composition A containing at least one compound chosen from C-glycosides, derivatives thereof and mixtures thereof, a composition B, conditioned separately from composition A, comprising at least one monosaccharide chosen from mannose, rhamnose and a mixture thereof.

Finally, the invention relates to a cosmetic or dermatological treatment process comprising at least one step of administration, in particular of topical application, to the skin and/or its integuments, of composition A and at least one step of administration, in particular of topical application to the skin and/or its integuments, of composition B.

The administration of composition A in according to the invention may be performed simultaneously with, or before or after, the administration of composition B. As specified previously, the administration of composition A and of composition B may be performed topically, orally or via injection.

According to one alternative, composition A is administered first and composition B is administered second. According to another alternative, composition B is administered first, and composition A is administered second.

Compositions A and B may be conditioned separately in two compartments, performed either by two separate containers, or inside a single device. The term "single device" means a device via which the two compartments are solidly attached. Such a device may be obtained via a process of monobloc moulding of the two compartments, especially made of a thermoplastic material. It may also result from any form of assembly, especially by bonding, welding or other click-fastening.

According to a first embodiment, the two containers are independent of each other. Such containers may be in various forms. They may especially be tubes, bottles or drums.

One and/or the other of the containers may be fitted with a manually operated pump on which is mounted a push button for actuating the pump and dispensing the composition via at least one dispensing orifice.

Alternatively, one and/or the other of the containers is pressurized, especially by means of a propellant, in particular a propellant gas. In this case, the container(s) is (are) equipped with a valve on which is mounted a push-button equipped with a nozzle or any other diffusion means for dispensing the product.

The propellant may be in a mixture with the composition to be dispensed or separated, especially via a piston that can slide inside the container, or via the flexible walls of a bag inside which the composition is placed.

The containers may be made of various materials: plastic, glass or metal.

Alternatively also, the two compartments are formed from two concentric compartments formed inside a tube, and mounted thereon is a pump with no air reuptake, and equipped with a push button with one or two dispensing orifices. Provided inside the tube is a piston that rises in the direction of the pump as and when the compositions are withdrawn from inside the containers. Such dispensing modes are especially used for dispensing toothpastes.

KEY TO THE FIGURES

FIG. 1: Diagram schematically representing the results obtained for the keratinocyte proliferation, in the presence of a control, in the presence of different markers, in medium deficient in growth factors, and with addition of different concentrations of L-rhamnose reported on the x-axis. The values reported on the y-axis correspond to the percentages of labelled cells measured relative to the control.

Figure 2:
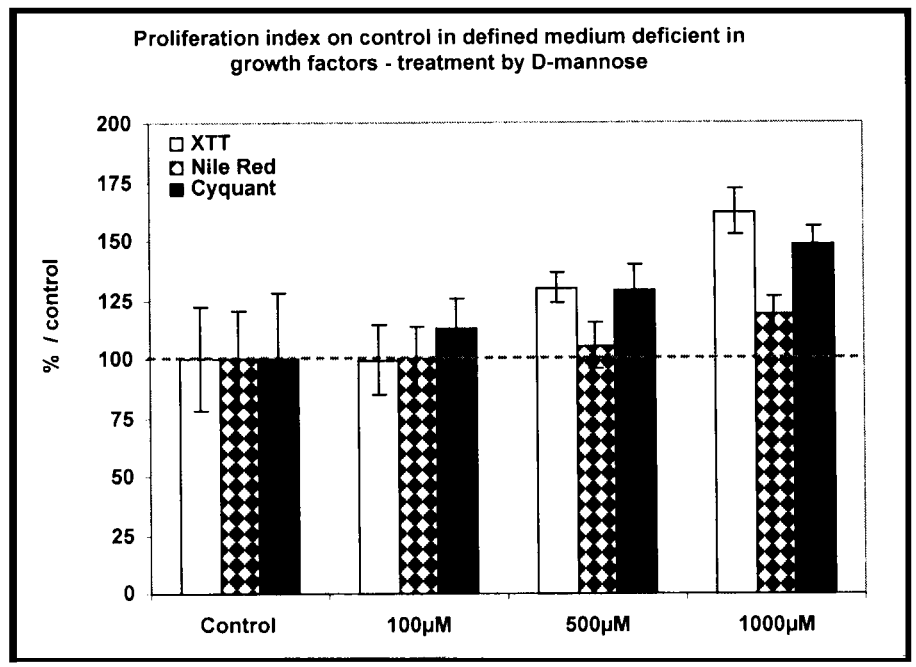
FIG. 2 shows the results obtained for the keratinocyte proliferation under certain conditions, described in more detail below. The values reported on the y-axis correspond to the percentages of labelled cells measured relative to the control.

FIG. 2: Diagram schematically representing the results obtained for the keratinocyte proliferation, in the presence of a control, in the presence of different markers, in medium deficient in growth factors, and with addition of different concentrations of D-mannose reported on the x-axis. The values reported on the y-axis correspond to the percentages of labelled cells measured relative to the control.

Figure 3:
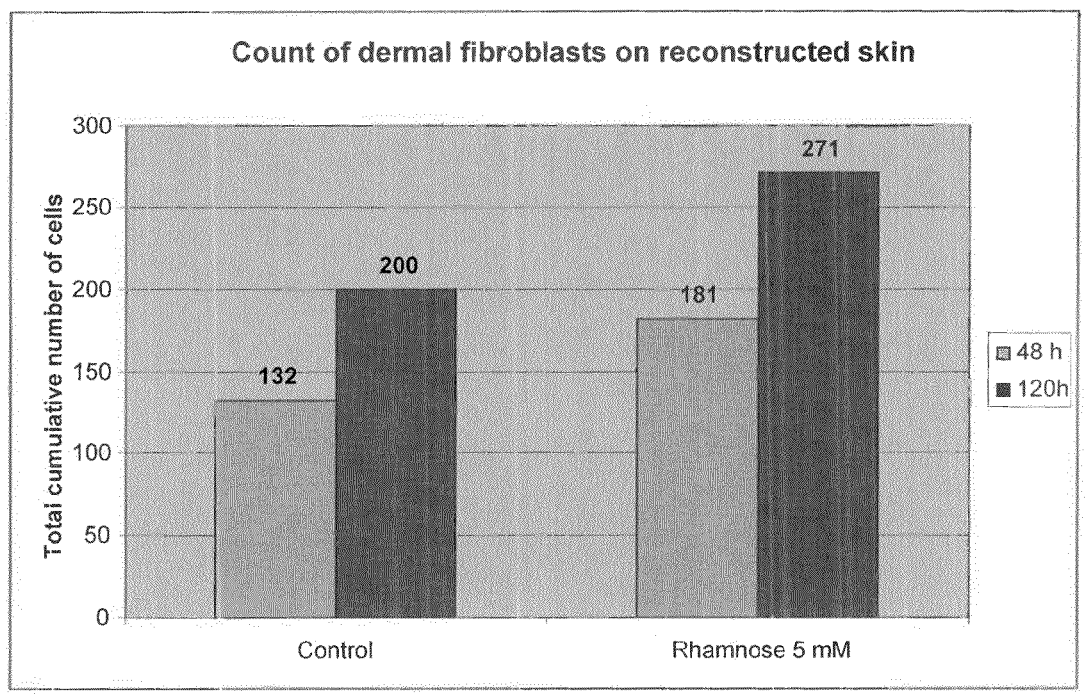
FIG. 3 shows the number of fibroblasts measured under certain conditions, described in more detail below.

FIG. 3: Diagram representing the number of fibroblasts measured between an untreated control whole reconstructed skin, on the left, and a whole reconstructed skin treated with 5 mM of rhamnose, on the right. The fibroblasts are counted at different stages of the treatment. Thus, for each skin type, the left-hand column corresponds to the count obtained at 48 hours and the right-hand column corresponds to the count obtained at 120 hours of treatment.

Figure 4:
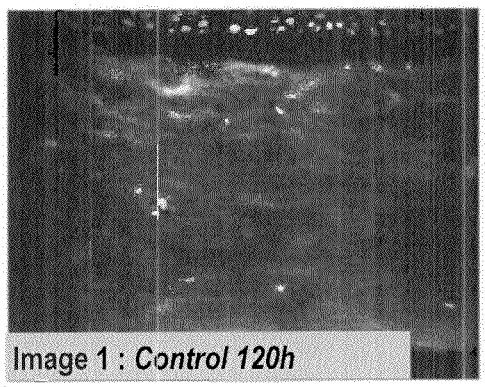
FIG. 4 shows photographs of frozen sections of reconstructed skin.
Figure 4:
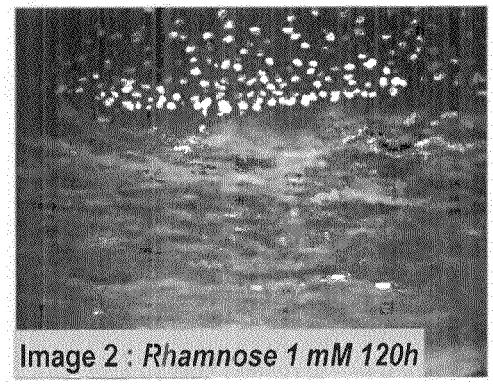

FIG. 4: Photographs of frozen sections of reconstructed skin 7 μm thick. The level of fluorescence is materialized by the white marks on the black and white photograph; it is proportional to the amount of type I procollagen. The control skin is on the left, and skin treated with 1 mM of rhamnose is on the right.

The invention is illustrated in greater detail in the examples that follow, which are given as non-limiting illustrations of the field of the invention.

EXAMPLES

Example 1

Proliferation of Keratinocytes

Protocol

The keratinocytes (HaCat line) are cultured under two conditions: whole defined culture medium (standard condition) and culture medium deficient in growth factors. This deficient medium gives rise to a controlled delay in cell proliferation. Under these conditions, it is then possible to measure the effects of compounds capable of compensating for the deficiency in growth factors of the culture medium and thus of relaunching the cell multiplication and/or of stimulating cell metabolism.

The keratinocyte proliferation is measured by means of three markers on the same cell population: the level of DNA, which is proportional to the number of cells (Cyquant probe), the level of constituent polar lipids of cell membranes (Nile red probe) and the mitochondrial respiration, which reflects the general cell metabolism (XTT probe).

Results

The results are given in FIGS. 1 and 2.

The two monosaccharides rhamnose and mannose demonstrate their capacity to activate keratinocyte proliferation when the keratinocytes are cultured in medium depleted in growth factors, a culturing condition that significantly delays their cell growth.

This activation of cell proliferation by the two compounds is manifested by a higher number of cells when compared with the untreated control.

This increased number of cells is materialized by a level of DNA (Cyquant), a level of polar lipids (Nile red signal) and a mitochondrial respiration (XTT signal) that are significantly increased when the monosaccharides are evaluated at 1 mM. At 500 µM, the two molecules already show efficacy. The two monosaccharides mannose and rhamnose thus exert an influence on keratinocyte proliferation. They activate the proliferation of keratinocytes cultured in medium depleted in growth factor, which is manifested by a higher number of cells when compared with an untreated control.

Rhamnose and mannose thus show anti-aging efficacy by boosting epidermal renewal and combating age-related epidermal atrophy.

Example 2

Proliferation of Fibroblasts

Protocol

Rhamnose was studied on a model of whole reconstructed skin in order to measure its anti-aging efficacy on the dermal compartment.

Briefly, the model of reconstructed skin used is that described by Bell et al. (Bell E. et al., *The reconstitution of living skin, J. Invest. Dermatol.,* 1983, July; 81): it includes a dermal equivalent on which is reconstructed a multistratified epidermis; the dermal equivalent is manufactured from acid-soluble collagen, culture medium containing serum and normal adult human fibroblasts. After 5 days of shrinkage, this equivalent is inoculated with keratinocytes and then cultured for 6 days in immersion and for 7 days in emersion in order to obtain a multistratified and differentiated epidermis having a horny layer.

The reconstructed skin is treated with 5 mM rhamnose for 2 days and 5 days in the culture medium; after the treatment, the reconstructed skins are included in Tissue Tek in order to produce frozen sections 7 µm thick with a cryostat. The sections produced are then stained with propidium iodide to label the DNA of the nuclei of the fibroblasts in order to count them. Three frozen sections are prepared at random on each reconstructed skin; on each section, two microscopic fields (25× objective lens) are analysed by fluorescence microscopy and photographed. The dermal fibroblasts are thus counted for each reconstructed skin on six images in total representing the six microscopic fields considered. The number of dermal fibroblasts is compared between the control skin and that treated with rhamnose at the two kinetic stages.

Results

The results are given in FIG. 3.

It was found that rhamnose induces stimulation of growth of the dermal fibroblasts of the reconstructed skin within 48 hours of treatment, this stimulation being confirmed at 120 hours of treatment, with between 30% and 35% additional cells (see FIG. 3). It should be noted that this stimulation is accompanied by a stimulation of procollagen 1 synthesis at 5 mM, and also at 1 mM, which may also result from the increased number of fibroblasts responsible for the secretion of this major protein of the extracellular matrix.

These two effects complement the anti-aging activity of rhamnose already measured on the epidermal compartment, by stimulating the proliferation and metabolism of the fibroblast, which is a major cell of the dermal compartment.

Example 3

Synthesis of Procollagen 1

Conventional detection via indirect immunofluorescence of type I procollagen in the dermis of the reconstructed skin was also performed on other series of frozen sections (anti-procoll 1 antibody (MAB 1912 Millipore)+FTIC-coupled conjugate (112-095-068 Jackson Immunoresearch)). In order to obtain bearings within the cutaneous architecture during the microscopic examination of the sections, the cell nuclei of the keratinocytes and fibroblasts are localized by staining them with propidium iodide, as described above. Three frozen sections are prepared at random on each reconstructed skin and on each section, and two microscopic fields (25× objective lens) are analysed by fluorescence microscopy and photographed. The levels of fluorescence proportional to the amount of type I procollagen are compared between the control skin and the skin treated with rhamnose.

In image 1, FIG. 4, corresponding to a section of control reconstructed skin at 120 hours of culture, the presence of type 1 procollagen synthesized by the dermal fibroblasts is materialized by the green fluorescence located in the bottom part of the image. The basal part of the epidermis, highly cellular tissue, which may be visualized by the numerous keratinocyte nuclei, can be made out in the top part of the image. The dermis, much less cellular tissue, also reveals the random distribution of the fibroblasts within the dermal extracellular matrix.

In image 2, FIG. 4, corresponding, for example, to a section of reconstructed skin treated with 1 mM rhamnose for 120 hours, a marked increase in green fluorescence is noted when compared with that observed for the control skin (image 1), and also a distribution of the fluorescent signal clearly materializing the fibrillar aspect of the newly synthesized type I procollagen. This increase in general fluorescence indicates that the rhamnose treatment has greatly stimulated the synthesis of type I procollagen by the fibroblasts.

These results clearly show the capacity of rhamnose to stimulate fibroblast metabolism, which metabolism, in the course of aging, becomes more imbalanced towards degradation of the extracellular matrix than towards its renewal.

By stimulating both the metabolism and growth of dermal fibroblasts, rhamnose clearly demonstrates its anti-aging efficacy on the dermis, this efficacy being complementary to that measured with respect to the epidermal compartment.

Example 4

Combination of Rhamnose and C-Xyloside,
Demonstration of the Complementarity of Action of
C-Xyloside and Rhamnose on the Cutaneous
Physiology Protocol Study the effects of addition of the C-xyloside/rhamnose combination on a reconstructed skin, the following was performed:

observation by microscope of a skin section with to immunohistochemical staining of the collagen IV and VII proteins; and observation of the epidermal thickness by histology after HES staining.

1. Preparation of the Reconstructed Skin

The reconstructed skin used is prepared according to the protocol described in Asselineau et al. (Models in Dermatol. Editions Loire and Mailbach, 1987, Vol III, 1-7). The changes to this protocol are:

the use of adult normal human dermal fibroblasts at a rate of $10^6$ cells per dermal equivalent;

the subculturing of the keratinocytes is performed at a rate of 50 000 cells per ring 1.5 cm in diameter. The keratinocytes used are obtained from the same donor and are in the first passage during the subculturing of the dermal equivalents;

the duration of the immersion phase is 7 days;

the duration of the emersion phase is 7 days.

2. Addition of C-Xyloside and Rhamnose

The culture is then placed in a crucible and treated in the culture medium with the C-xyloside/rhamnose combination for 5 days, the medium being changed every two days.

3.a. Analysis of Collagens IV and VII

The analysis of the reconstructed skins is performed at the end of the treatment. A control sample (absence of C-xyloside and rhamnose) is systematically prepared and analysed in parallel.

Each skin sample is divided into two half moons, one for the histological analysis, the other for the immunohistochemistry on 5 µm frozen sections. The standard technique of indirect immunofluorescence is performed with an anti-collagen VII monoclonal antibody (LH7.2, Chemicon International Inc., USA) and a fluoro scene-coupled conjugate (FITC-conjugated rabbit anti-mouse immunoglobulins, DAKO, Denmark), and a conjugate coupled to Alexa 488 (A 11017 Invitrogen). The cell nuclei are stained with propidium bromide so as to clearly locate the various compartments of the reconstructed skin.

3.b. Analysis of the Epidermal Proliferation

The second half of the half moons is included in paraffin in order to make paraffin sections 5 µm thick; the sections are then stained with HES stain.

The sections are analysed by standard microscopy on a light background. The epidermal proliferation is quantified by counting the keratinocyte layers and by measuring the total thickness of the malpighian epidermis, this being done by comparing the epidermis of the control skin with that of the skin treated with the C-xyloside/rhamnose combination. The whole analysis is performed on a Zeiss image analysis station+KS 300 software.

Results

An increase in the thickness of the epidermis, reinforcement of the structure of the dermal epidermal junction, and an increased proliferation of dermal fibroblasts are observed.

These effects, obtained with the combination of rhamnose and C-xyloside, lead to regeneration of the skin by acting on its between main compartments, thus demonstrating overall anti-aging activity.

Example 5

Example of Preparation of a Cosmetic Composition According to the Invention

| Epidermal and dermal regenerating creams: oil-in-water emulsion | |
|---|---|
| Ammonium Polyacryldimethyltauramide (Hostacerin AMPS from Clariant) | 1.00% |
| Cyclohexasiloxane | 5.0% |
| Apricot kernel oil | 7% |
| Isononyl isononanoate | 7% |
| Stearyl alcohol | 0.30% |
| Glyceryl stearate/PEG-100 stearate | 0.70% |
| Dimyristyl tartrate/cetearyl alcohol/C12-15 pareth-7/PPG-25 laureth-25 | 0.50% |
| Xanthan gum | 0.20% |
| Rhamnose | 5% |
| C-Xyloside | 3% |
| Preserving agents | 0.50% |
| Water | qs 100 |

Example 6

Example of Preparation of a Cosmetic Composition According to the Invention

| Epidermal regeneration creams: oil-in-water emulsion | |
|---|---|
| Ammonium Polyacryldimethyltauramide (Hostacerin AMPS from Clariant) | 1.00% |
| Cyclohexasiloxane | 5.0% |
| Glycerol | 1.70% |
| Stearyl alcohol | 0.30% |
| Apricot kernel oil | 7% |
| Isononyl isononanoate | 7% |
| Dimyristyl tartrate/cetearyl alcohol/C12-15 pareth-7/PPG-25 laureth-25 | 0.50% |
| Xanthan gum | 0.20% |
| Mannose | 5% |
| C-Xyloside | 5% |
| Preserving agents | 0.50% |
| Water | qs 100 |

Example 7

Example of Preparation of a Cosmetic Composition According to the Invention

Anti-Aging Facial Day Cream

| Phase A1: | |
|---|---|
| Sucrose distearate sold by the company Stéarinerie Dubois | 1.75% |
| Sorbitan stearate oxyethylenated with 4 mol of ethylene oxide, sold by the company ICI under the name Tween 61 | 1.15% |
| Stearic acid | 0.75% |
| Stearyl heptanoate | 4.00% |
| Petroleum jelly codex | 1.50% |
| Avocado oil | 3.20% |
| Jojoba oil | 3.00% |
| Volatile silicone oil | 2.70% |
| Vitamin E acetate | 1.00% |
| Vitamin F glycerides | 3.00% |
| Phase A2: | |
| Silicone gum sold by Dow Corning under the name Q2-1403 Fluid | 3.00% |
| Propyl paraben | 0.2% |
| Fragrance | 0.3% |
| Phase B: | |
| Glycerol | 3.00% |
| Hydroxyproline | 1.00% |

-continued

| | |
|---|---|
| D-Panthenol | 1.00% |
| Triethanolamine | 0.35% |
| Rhamnose | 3.00% |
| C-Xyloside | 10.00% |
| Methyl paraben | 0.3% |
| Demineralized water | qs 100% |
| Phase C: | |
| Ammonium Polyacryldimethyltauramide (Hostacerin AMPS from Clariant) | 1% |

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials. Terms such as "contain(s)" and the like as used herein are open terms meaning 'including at least' unless otherwise specifically noted. The term "mentioned" notes exemplary embodiments, and is not limiting to certain species. As used herein the words "a" and "an" and the like carry the meaning of "one or more."

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A composition comprising, in a physiologically acceptable medium, at least one monosaccharide selected from the group consisting of mannose and rhamnose, wherein the monosaccharide is present as a monomer, and at least one additional compound chosen from C-glycosides of formula (I):

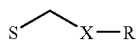
(I)

in which:
R represents:
a saturated $C_1$-$C_{20}$ or unsaturated $C_2$-$C_{20}$ linear alkyl radical, or a saturated or unsaturated, branched or cyclic $C_3$-$C_{20}$ alkyl radical;
a saturated $C_1$-$C_{20}$ or unsaturated $C_2$-$C_{20}$ linear, or saturated or unsaturated, branched or cyclic $C_3$-$C_{20}$ hydrofluoroalkyl or perfluoroalkyl radical; the hydrocarbon-based chain constituting said radicals optionally being interrupted with 1 or more heteroatoms chosen from:
oxygen,
sulfur,
nitrogen, and
silicon,
and optionally being substituted with at least one radical chosen from:
—$OR_4$,
—$SR_4$,
—$NR_4R_5$,
—$COOR_4$,
—$CONHR_4$,
—CN,
a halogen atom,
a $C_1$-$C_6$ hydrofluoroalkyl or perfluoroalkyl radical, and/or
$C_3$-$C_8$ cycloalkyl radical,
with $R_4$ and $R_5$ representing, independently of each other, a hydrogen atom or a saturated $C_1$-$C_{30}$ or unsaturated $C_2$-$C_{30}$ linear, or a saturated or unsaturated, branched or cyclic $C_3$-$C_{30}$ alkyl, perfluoroalkyl or hydrofluoroalkyl radical; or a $C_6$-$C_{10}$ aryl radical,
X represents a radical chosen from:

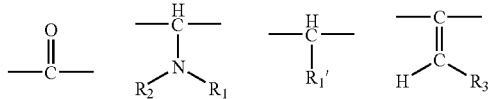

with $R_1$, $R_2$ and $R_3$ representing, independently of each other, a hydrogen atom or a radical R, with R as defined above, and $R'_1$ represents a hydrogen atom, an —OH group or a radical R as defined above, $R_1$ optionally also denoting a $C_6$-$C_{10}$ aryl radical;
S represents a xylose sugar moiety in pyranose or furanose form of L or D configuration, and
the bond S—$CH_2$—X represents a bond of C-anomeric nature, which may be α or β,
and the cosmetically acceptable salts and isomers thereof.

2. A composition according to claim 1, in which S represents D-xylose.

3. A composition according to claim 2, in which X represents a group chosen from —CO—, —CH(OH)— and —CH (NH2).

4. A composition according to claim 3, in which R denotes a linear C1-C4 alkyl radical, optionally substituted with —OH, —COOH or —COOR"2, R"2 being a C1-C4 saturated alkyl radical.

5. A composition according to claim 1, comprising at least one C-glycoside chosen from C-[β]-xylopyranoside-n-propane-2-one, C-[α]-D-xylopyranoside-n-propane-2-one, C-[β]-D-xylopyranoside-2-hydroxypropane, C-[α]-D-xylopyranoside-2-hydroxypropane isomers thereof and mixtures thereof.

6. A composition according claim 1, in which the amount of the monosaccharide(s) is 0.001%-30% by weight relative to the total weight of the composition.

7. A composition according to claim 1, in which the amount of the said additional compound(s) is 0.001%-30% by weight relative to the total weight of the composition.

8. A method of treating signs of ageing of the skin or its integuments comprising applying the composition of claim 1 to human skin and/or its integuments.

9. A method for improving the radiance of the complexion, for reducing wrinkles and/or fine lines, for improving and/or decreasing the microrelief of the skin, for making the skin smooth and/or for improving the mechanical properties of the skin and/or for increasing the resistance of the skin to mechanical attack, and/or for promoting skin repair comprising applying the composition of claim 1 to human skin in need thereof.

10. A method for improving the density and firmness of the skin and/or the cohesion of its various compartments comprising applying the composition of claim 1 to human skin in need thereof.

11. A method for treating wrinkles and/or fine lines, withered skin, lack of skin elasticity and/or tonicity, thinning of the dermis, degradation of collagen fibres, flaccid skin, thinned skin and/or any internal degradation of the skin caused by exposure to ultraviolet radiation comprising applying the composition of claim 1 to human skin in need thereof.

12. A method for stimulating the synthesis of glycosaminoglycans containing D-glucosamine and/or N-acetyl-D-glucosamine residue, and/or proteoglycans, by the fibroblasts and/or keratinocytes comprising applying the composition of claim 1 to human skin in need thereof.

13. A method for increasing the synthesis of laminins and the synthesis of collagens comprising applying the composition of claim 1 to human skin in need thereof.

14. A device comprising a combination of at least one monosaccharide selected from the group consisting of mannose and rhamnose and at least one additional compound selected from the group consisting of chosen from C-glycosides and C-glycoside derivatives of formula I as defined in claim 1, the device being suitable for intraepidermal and/or intradermal and/or subcutaneous injection of said combination.

15. A composition according to claim 1, in which S represents D-xylose and X represented a —CH(OH)— group.

16. A composition according to claim 1, wherein S represents D-xylose, X represents a group chosen from —CO—, —CH(OH)— and —CH(NH2)-, and R denotes a linear C1-C2 alkyl radical.

17. A composition according to claim 16, wherein R is a methyl radical.

18. A composition according to claim 1, wherein the C-glycoside of formula I is chosen from C-[β]-D-xylopyranoside-2-hydroxypropane and C-[α]-D-xylopyranoside-2-hydroxypropane.

* * * * *